US012042250B2

(12) United States Patent
McCulloch et al.

(10) Patent No.: US 12,042,250 B2
(45) Date of Patent: Jul. 23, 2024

(54) COMPOSITIONS, DEVICES AND METHODS FOR DIAGNOSING HEART FAILURE AND FOR PATIENT-SPECIFIC MODELING TO PREDICT OUTCOMES OF CARDIAC RESYNCHRONIZATION THERAPY

(71) Applicant: The Regents Of The University Of California, Oakland, CA (US)

(72) Inventors: Andrew D. McCulloch, San Diego, CA (US); Adarsh Krishnamurthy, San Diego, CA (US); Christopher Villongco, San Diego, CA (US); David Krummen, San Diego, CA (US); Sanjiv Narayan, San Diego, CA (US); Jeffrey Omens, San Diego, CA (US); Roy Kerckhoffs, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/036,414

(22) PCT Filed: Nov. 14, 2014

(86) PCT No.: PCT/US2014/065841
§ 371 (c)(1),
(2) Date: May 12, 2016

(87) PCT Pub. No.: WO2015/073927
PCT Pub. Date: May 21, 2015

(65) Prior Publication Data
US 2016/0262635 A1    Sep. 15, 2016

Related U.S. Application Data

(60) Provisional application No. 61/905,138, filed on Nov. 15, 2013.

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/7275* (2013.01); *A61B 6/503* (2013.01);
(Continued)

(58) Field of Classification Search
CPC .... A61B 6/507; A61B 5/02028; A61N 1/3627
See application file for complete search history.

(56) References Cited

U.S. PATENT DOCUMENTS 5,273,038 A    12/1993    Beavin
6,501,979 B1   12/2002    Manning et al.
(Continued)

FOREIGN PATENT DOCUMENTS

WO    WO-2004102482 A1    11/2004
WO    WO-2005072607 A1    8/2005
(Continued)

OTHER PUBLICATIONS

Ilardi et al., Myocardial Work by Echocardiography: Principles and Application in Clinical Practice, 2021, Clinical Medicine, 10, 1-16. (Year: 2021).*
(Continued)

*Primary Examiner* — Rex R Holmes
*Assistant Examiner* — Jennifer L Ghand
(74) *Attorney, Agent, or Firm* — Mintz Levin Cohn Ferris Glovsky and Popeo, P.C.

(57) ABSTRACT

In alternative embodiments, provided are compositions, medical devices or products of manufacture, systems, diagnostic tools, and methods, including computer implemented methods, for predicting the response of patients with dyssynchronous heart failure (DHF) to cardiac resynchro-
(Continued)

Figure 3: Different components of the patient-specific electromechanics model utilized in its construction.

nization therapy (CRT), comprising: measuring or determining the fraction of the LV/septum performing negative work (MNW); and measuring or determining the coefficient of variation of external work density (COVW), wherein the MNW fraction performing negative work and coefficient of variation COVW (sd/mean) correlated strongly with observed reduction in end-systolic volume after CRT. In alternative embodiments, provided are products comprising a remote communication device for remotely and operably interacting with a programmable implantable cardioverter-defibrillator (ICD) or CRT-D including a defibrillator in case defibrillation is needed, an implantable defibrillator, a dual-chamber defibrillator or a single-chamber defibrillator, or a CRT-P where there is no defibrillator but the CRT-P has a pacing system alone without the defibrillator.

21 Claims, 15 Drawing Sheets

(51) Int. Cl.
*A61B 6/50* (2024.01)
*A61B 8/08* (2006.01)
*A61N 1/362* (2006.01)
*A61N 1/39* (2006.01)
*G09B 23/30* (2006.01)
*G16H 50/50* (2018.01)
*G16Z 99/00* (2019.01)
*A61B 5/0215* (2006.01)
*A61B 5/029* (2006.01)
*A61B 5/349* (2021.01)
*A61B 6/03* (2006.01)

(52) U.S. Cl.
CPC ............ *A61B 6/507* (2013.01); *A61B 8/0883* (2013.01); *A61B 8/48* (2013.01); *A61B 8/483* (2013.01); *A61B 8/485* (2013.01); *A61B 8/5223* (2013.01); *A61N 1/3621* (2013.01); *A61N 1/3627* (2013.01); *A61N 1/395* (2013.01); *G09B 23/303* (2013.01); *G16H 50/50* (2018.01); *G16Z 99/00* (2019.02); *A61B 5/0215* (2013.01); *A61B 5/029* (2013.01); *A61B 5/349* (2021.01); *A61B 6/032* (2013.01); *A61B 2576/023* (2013.01)

(56) References Cited

U.S. PATENT DOCUMENTS

| | | | |
|---|---|---|---|
| 7,010,347 | B2 | 3/2006 | Schecter |
| 7,286,871 | B2 | 10/2007 | Cohen |
| 7,526,338 | B1 | 4/2009 | Gill et al. |
| 8,521,266 | B2 | 8/2013 | Narayan et al. |
| 9,211,110 | B2 | 12/2015 | Rubin et al. |
| 9,706,935 | B2 | 7/2017 | Spector |
| 10,315,144 | B2 | 6/2019 | Reichter et al. |
| 10,556,113 | B2 | 2/2020 | Villongco et al. |
| 10,856,816 | B2 | 12/2020 | Villongco |
| 2002/0035334 | A1 | 1/2002 | Ooishi et al. |
| 2004/0015081 | A1 | 1/2004 | Kramer et al. |
| 2004/0176697 | A1 | 1/2004 | Li et al. |
| 2007/0016108 | A1 | 1/2007 | Bewlay et al. |
| 2007/0032733 | A1 | 1/2007 | Yasuda |
| 2007/0259031 | A1 | 2/2007 | Kong et al. |
| 2007/0270703 | A1 | 2/2007 | Szeto et al. |
| 2008/0021336 | A1 | 1/2008 | Dobak |
| 2009/0048513 | A1* | 2/2009 | Friedman ............... A61B 8/00 600/437 |
| 2009/0306732 | A1* | 12/2009 | Rosenberg ........... A61B 5/0422 607/9 |
| 2010/0016917 | A1 | 1/2010 | Efimov et al. |
| 2010/0152796 | A1 | 6/2010 | Schecter |
| 2010/0280355 | A1* | 11/2010 | Grimm .............. A61B 5/02028 600/437 |
| 2010/0298904 | A1 | 11/2010 | Blomqvist et al. |
| 2011/0251504 | A1 | 10/2011 | Tereshchenko et al. |
| 2011/0251505 | A1 | 10/2011 | Narayan et al. |
| 2011/0307231 | A1 | 12/2011 | Kirchner et al. |
| 2011/0311116 | A1 | 12/2011 | Benn |
| 2012/0035459 | A1 | 2/2012 | Revishvili et al. |
| 2012/0087563 | A1 | 4/2012 | Ionasec et al. |
| 2012/0165674 | A1* | 6/2012 | Abe ..................... A61B 8/0883 600/443 |
| 2012/0283587 | A1 | 11/2012 | Gosh et al. |
| 2013/0006131 | A1 | 1/2013 | Narayan et al. |
| 2013/0034203 | A1 | 2/2013 | Wang et al. |
| 2013/0096394 | A1 | 4/2013 | Gupta et al. |
| 2013/0131529 | A1 | 5/2013 | Jia et al. |
| 2013/0158557 | A1 | 6/2013 | Komistek |
| 2013/0197881 | A1* | 8/2013 | Mansi .................. A61N 1/3627 703/2 |
| 2013/0211256 | A1 | 8/2013 | Russell et al. |
| 2014/0005562 | A1 | 1/2014 | Bunch et al. |
| 2014/0088943 | A1* | 3/2014 | Trayanova ............. A61B 5/042 703/11 |
| 2014/0107510 | A1 | 4/2014 | Bogun et al. |
| 2014/0200575 | A1 | 7/2014 | Spector |
| 2014/0241988 | A1 | 8/2014 | Jalife |
| 2014/0276152 | A1 | 9/2014 | Narayan et al. |
| 2014/0323882 | A1 | 10/2014 | Ghosh et al. |
| 2015/0042646 | A1 | 2/2015 | Comaniciu et al. |
| 2015/0216432 | A1 | 8/2015 | Yang |
| 2015/0216434 | A1 | 8/2015 | Ghosh et al. |
| 2015/0216438 | A1 | 8/2015 | Bokan et al. |
| 2015/0313510 | A1 | 11/2015 | Razavi et al. |
| 2015/0329907 | A1* | 11/2015 | Das ..................... C12Q 1/6883 514/44 A |
| 2016/0005106 | A1 | 1/2016 | Giraldez et al. |
| 2016/0012592 | A1 | 1/2016 | Chou et al. |
| 2016/0022375 | A1 | 1/2016 | Blake et al. |
| 2016/0135702 | A1 | 5/2016 | Perez |
| 2016/0157769 | A1 | 6/2016 | Min et al. |
| 2016/0210435 | A1 | 7/2016 | Neumann et al. |
| 2016/0262635 | A1* | 9/2016 | McCullouch ........ A61B 8/5223 |
| 2016/0331337 | A1 | 11/2016 | Ben-Haim |
| 2017/0027649 | A1 | 2/2017 | Kiraly et al. |
| 2017/0079542 | A1 | 3/2017 | Spector |
| 2017/0178403 | A1 | 6/2017 | Krummen et al. |
| 2017/0185740 | A1* | 6/2017 | Seegerer .............. A61B 5/0452 |
| 2017/0209698 | A1 | 7/2017 | Villongco et al. |
| 2017/0304005 | A1 | 10/2017 | Maino et al. |
| 2017/0319278 | A1 | 11/2017 | Trayanova et al. |
| 2017/0367603 | A1 | 12/2017 | Spector |
| 2018/0028265 | A1 | 2/2018 | Azevedo Da Silva et al. |
| 2018/0055401 | A1 | 3/2018 | Wang et al. |
| 2018/0318606 | A1 | 11/2018 | Robinson et al. |
| 2019/0104951 | A1 | 4/2019 | Valys et al. |
| 2019/0206127 | A1 | 7/2019 | Krummen et al. |
| 2019/0282821 | A1 | 9/2019 | Masuda et al. |
| 2019/0304183 | A1 | 10/2019 | Krummen et al. |
| 2020/0138394 | A1 | 5/2020 | Vanden Berghe et al. |
| 2020/0245935 | A1 | 8/2020 | Krummen et al. |

FOREIGN PATENT DOCUMENTS

| | | | |
|---|---|---|---|
| WO | WO 2009079344 A1 | 6/2009 | |
| WO | WO-2010042826 A1 | 4/2010 | |
| WO | WO-2010052303 A1 | 5/2010 | |
| WO | WO-2010054409 A1 | 5/2010 | |
| WO | WO-2012055498 A1 * | 5/2012 | ........... A61B 5/0044 |
| WO | WO-2012/109618 A2 | 8/2012 | |

OTHER PUBLICATIONS

Voigt et al., 2- and 3-Dimensional Myocardial Strain in Cardiac Health and Disease, Nov. 2019, JACC: Cardiovascular Imaging, vol. 12, 1849-1863. (Year: 2019).*

(56) References Cited

OTHER PUBLICATIONS

Aguado-Sierra, Jazmin, et al., "Patient-specific modeling of dyssynchronous heart failure: a case study." *Progress in biophysics and molecular biology* 107.1 (2011): 147-155.
Kerckhoffs, Roy, et al., "Ventricular dilation and electrical dyssynchrony synergistically increase regional mechanical non-uniformity but not mechanical dyssynchrony: a computational model." *Circulation: Heart Failure* (2010): Circheartfailure-109.
Krishnamurthy, Adarsh, et al., "Patient-specific models of cardiac biomechanics." *Journal of computational physics* 244 (2013): 4-21.
Strauss, David G., et al., "Defining left bundle branch block in the era of cardiac resynchronization therapy." *American Journal of Cardiology* 107.6 (2011): 927-934.
Villongco, Christopher T., et al., "Patient-specific modeling of ventricular activation pattern using surface ECG-derived vectorcardiogram in bundle branch block." *Progress in biophysics and molecular biology* 115.2-3 (2014): 305-313.
Seo, Yoshihiro, et al., "Mechanical dyssynchrony assessed by speckle tracking imaging as a reliable predictor of acute and chronic response to cardiac resynchronization therapy." *Journal of the American Society of Echocardiography* 22.7 (2009): 839-846.
Kirn, Borut, et al., "Mechanical discoordination rather than dyssynchrony predicts reverse remodeling upon cardiac resynchronization." Am J Physiol Heart Circ Physiol. 295, Aug. 2008;295(2):H640-6, 7 pages.
Helm, Robert H. et al., "Cardiac Dyssynchrony Analysis Using Circumferential Versus Longitudinal Strain: Implications for Assessing Cardiac Resynchronization." Circulation. 111 (2005), pp. 2760-2767, 8 pages.
Leclercq, Christophe, et al., "Systolic Improvement and Mechanical Resynchronization Does Not Require Electrical Synchrony in the Dilated Failing Heart With Left Bundle-Branch Block." Circulation, 106 (2002). pp. 1760-1763, 4 pages.
De Boeck, Bart W. L. et al., "Septal rebound stretch reflects the functional substrate to cardiac resynchronization therapy and predicts volumetric and neurohormonal response." Eur J Heart Fail. 2009;1 1(9):863-71, 9 pages.
Niederer, Steven Alexander, et al., "Analyses of the Redistribution of Work following Cardiac Resynchronisation Therapy in a Patient Specific Model." PLoS One 7(8), 2012, 9 pages.
Alexander, D. C., et al. "Spatial Transformations of Diffusion Tensor Magnetic Resonance Images." *IEEE Transactions on Medical Imaging*, vol. 20 No. 11, 2001, pp. 1131-1139.
Aronszajn, N. "Theory of reproducing kernels." *Transactions of the American Mathematical Society*, vol. 68, 1950, pp. 337-404.
Arsigny, V., et al. "Log-Euclidean metrics for fast and simple calculus on diffusion tensors." *Magnetic Resonance in Medicine : Official Journal of the Society of Magnetic Resonance in Medicine / Society of Magnetic Resonance in Medicine*, vol. 56 No. 2, 2006, pp. 411-421.
Auricchio, A., et al. "Characterization of left ventricular activation in patients with heart failure and left bundle-branch block." *Circulation*, vol. 109, No. 9, 2004, pp. 1133-1139.
Bazan, V., et al., "Three-dimensional myocardial scar characterization from the endocardium: Usefulness of endocardial unipolar electroanatomic mapping." J Cardiovasc Electrophysiol 2019;30:427-437.
Berger, T., et al."Single-beat noninvasive imaging of cardiac electrophysiology of ventricular pre-excitation." *Journal of the American College of Cardiology*, vol. 48, No. 10, 2006, pp. 2045-2052.
Burger, H. C., et al., "Heart-Vector and Leads." British Heart Journal, vol. 8, No. 3, 1946, pp. 157-161.
Cao, Y., et al. "Large deformation diffeomorphic metric mapping of vector fields." *Medical Imaging, IEEE Transactions*, vol. 24, No. 9, 2005, pp. 1216-1230.
Carrault, G., et al., "A model-based approach for learning to identify cardiac arrhythmias." Joint European Conference on Artificial Intelligence in Medicine and medical Decision Making. Springer, Berlin, Heidelberg, 1999. (Year: 1999).

Carrault, G., et al., "Temporal abstraction and inductive logic programming for arrhythmia recognition from electrocardigrams." Artificial intelligence in medicine 28.3 (2003): 231-263. (Year: 2003).
Chalil, S., et al., "Intraventricular Dyssynchrony Predicts Mortality and Morbidity After Cardiac Resynchronization Therapy A Study Using Cardiovascular Magnetic Resonance Tissue Synchronization Imaging", Journal of The American College Of Cardiology, vol. 50, No. 3, pp. 243-252, XP029654014, ISSN: 0735-1097, DOI: 10.1016/J.JACC. 2007.03.035.
Cluitmans, M. J. M., et al. "Inverse Reconstruction of Epicardial Potentials Improve by Vectorcardiography and Realistic Potentials." *Computing in Cardiology*, vol. 40, 2013, pp. 369-372.
Cobb, L.A., et al., "Changing incidence of out-of-hospital ventricular fibrillation, 1980-2000." Jama 288.23 (2002): 3008-3013.
Coronel, R., et al., "Right ventricular fibrosis and conduction delay in a patient with clinical signs of Brugada syndrome: a combined electrophysiological, genetic, histopathologic, and computational study." Circulation. 2005;112:2769-77.
Cortez, D.L. et al., "When deriving the spatial QRS-T angle from the 12-lead electrocardiogram, which transform is more Frank: regression or inverse Dower?" Journal of Electrocardiology 43.4 (2010): 302-309.
Daubert, J.-C., et al. "2012 EHRA/HRS expert consensus statement on cardiac resynchronization therapy in heart failure: implant and follow-up recommendations and management." *Heart Rhythm : The Official Journal of the Heart Rhythm Society*, vol. 9 No. 9, 2012, pp. 1524-1576.
De Vito, E., et al. "Adaptive kernel methods using the balancing principle." *Foundations of Computational Mathematics*, vol. 10, No. 4, 2010, pp. 455-479.
De Vito, E., et al. "Learning from examples as an inverse problem." *Journal of Machine Learning Research*, vol. 6, 2005, pp. 883-904.
Dossel, O., et al. "Imaging of bioelectric sources in the heart using a cellular automaton model." *Conference Proceedings : Annual International Conference of the IEEE Engineering in Medicine and Biology Society. IEEE Engineering in Medicine and Biology Society. Conference*, 2005, pp. 1067-1070.
Edenbrandt, L., et al., "Vectorcardiogram synthesized from a 12-lead ECG: superiority of the inverse Dower matrix." Journal of Electrocardiology, vol. 21, No. 4, 1988, pp. 361-367.
Engl, H., et al. "Regularization of Inverse Problems." *Mathematics and Its Application*, vol. 375, 1996.
Epstein A.E., et al., ACC/AHA/HRS 2008 Guidelines for Device-Based Therapy of Cardiac Rhythm AbnormalitiesPractice Guideline. J Am Coll Cardiol. 2008;51:21.
Epstein A.E., et al., American College of Cardiology F, American Heart Association Task Force on Practice G and Heart Rhythm S. 2012 ACCF/AHA/HRS focused update incorporated into the ACC/AHA/HRS 2008 guidelines for device-based therapy of cardiac rhythm abnormalities: a report of the American College of Cardiology Foundation/American Heart Association Task Force on Practice Guidelines and the Heart Rhythm Society. J Am Coll Cardiol. 2013;61:e6-75.
Fillard, P., et al., "Clinical DT-MRI estimation, smoothing, and fiber tracking with log-Euclidean metrics." IEEE Transactions on Medical Imaging, vol. 26, No. 11, 2007, pp. 1472-1482.
Gersh B.J., et al., 2011 ACCF/AHA Guideline for the Diagnosis and Treatment of Hypertrophic Cardiomyopathy: a report of the American College of Cardiology Foundation/American Heart Association Task Force on Practice Guidelines. Developed in collaboration with the American Association for Thoracic Surgery, American Society of Echocardiography, American Society of Nuclear Cardiology, Heart Failure Society of America, Heart Rhythm Society, Society for Cardiovascular Angiography and Interventions, and Society of Thoracic Surgeons. Journal of the American College of Cardiology. 2011;58:e212-60.
Gold, M. R., et al. "The relationship between ventricular electrical delay and left ventricular remodelling with cardiac resynchronization therapy." *European Heart Journal*, vol. 32, No. 20, 2011, pp. 2516-2524.

(56) References Cited

OTHER PUBLICATIONS

Golub, G. H., et al., "Singular Value Decomposition and Least Squares Solutions." Numerische Mathematik, vol. 14, 1970, pp. 403-420.

Gonzales, M. J., et al. "A three-dimensional finite element model of human atrial anatomy: new methods for cubic Hermite meshes with extraordinary vertices." *Medical Image Analysis*, vol. 17 No. 5, 2013, pp. 525-537.

Gonzales, M.J., et al., "Structural contributions to fibrillatory rotors in a patient-derived computational model of the atria." EP Europace 16.suppl 4 (2014): iv3-iv10.

Greensite, F., et al., "An improved method for estimating epicardial potentials from the body surface." IEEE Transactions on Bio-Medical Engineering, vol. 45, No. 1, 1998, pp. 98-104.

Guillem, M. S., et al. "Derivation of orthogonal leads from the 12-lead ECG. Accuracy of a single transform for the derivation of atrial and ventricular waves." *In Computers in Cardiology*, 2006, pp. 249-252.

Gulrajani, R.M., "The forward and inverse problems of electrocardiography." IEEE Engineering in Medicine and Biology Magazine 17.5 (1998): 84-101.

Haissaguerre, M., et al., "Localized Structural Alterations Underlying a Subset of Unexplained Sudden Cardiac Death." Circ Arrhythm Electrophysiol 2018;11:e006120.

Han, C., et al. "Noninvasive reconstruction of the three-dimensional ventricular activation sequence during pacing and ventricular tachycardia in the canine heart." *American Journal of Physiology. Heart and Circulatory Physiology*, vol. 302, No. 1, 2012, pp. H244-H252.

Han, C., et al. "Noninvasive reconstruction of the three-dimensional ventricular activation sequence during pacing and ventricular tachycardia in the rabbit heart." *Conference Proceedings : Annual International Conference of the IEEE Engineering in Medicine and Biology Society*, 2011, pp. 1684-1687.

He, B., et al. "Noninvasive three-dimensional activation time imaging of ventricular excitation by means of a heart-excitation model." *Physics in Medicine and Biology*, vol. 47, No. 22, 2002, pp. 4063-4078.

Ho, G., et al., "Rotors exhibit greater surface ECG variation during ventricular fibrillation than focal sources due to wavebreak, secondary rotors, and meander." J Cardiovasc Electrophysiol. 2017;28:1158-1166.

Hren, R., et al., "Value of simulated body surface potential maps as templates in localizing sites of ectopic activation for radiofrequency ablation." Physiological measurement 18.4 (1997): 373-400.

Kimeldorf, G., et al., "Some results on Tchebycheffian spline functions." Journal of Mathematical Analysis and Applications, vol. 33, 1971, pp. 82-95.

Kindermann, S., et al., "On the convergence of the quasi-optimality criterion for (iterated) Tikhonov regularization." Inverse Problems and Imaging, vol. 2, No. 2, 2008, pp. 291-299.

Kors, J. A., et al. "Reconstruction of the Frank vectorcardiogram from standard electrocardiographic leads: diagnostic comparison of different methods." *European Heart Journal*, vol. 11, No. 12, 1990, pp. 1083-1092.

Krishnamurthy, A., et al., "CRT Response is Greater in Patients With Larger Fraction of the Myocardium Performing Negative Regional Work." Circulation 128.Suppl 22 (2013): A11135-A11135, Abstract only.

Krummen, D.E., et al., "Mechanisms of human atrial fibrillation initiation: clinical and computational studies of repolarization restitution and activation latency." Circ Arrhythm Electrophysiol 2012;5:1149-59.

Krummen, D.E., et al., "Modifying Ventricular Fibrillation by Targeted Rotor Substrate Ablation: Proof-of-Concept from Experimental Studies to Clinical Vf." J Cardiovasc Electrophysiol 2015;26:1117-26.

Krummen, D.E., et al., "Rotor stability separates sustained ventricular fibrillation from self-terminating episodes in humans." Journal of the American College of Cardiology 63.24 (2014): 2712-2721.

Li, G., et al., "Localization of the site of origin of cardiac activation by means of a heart-model-based electrocardiographic imaging approach." IEEE Transactions on Bio-Medical Engineering, vol. 48, No. 6, 2001, pp. 660-669.

Lin, T., et al. "Implant electrical characteristics predict response to cardiac resynchronization therapy." *World Journal of Cardiovascular Diseases*, 2014.

Liu, C., et al. "Estimation of global ventricular activation sequences by noninvasive 3-dimensional electrical imaging: validation studies in a swine model during pacing." *Journal of Cardiovasc Electrophysiol*, vol. 19, No. 5, 2009, pp. 535-540.

McVeigh, E.R., et al., "Regional myocardial strain measurements from 4DCT in patients with normal LV function." J Cardiovasc Comput Tomogr 2018;12:372-378.

Messinger-Rapport, B. J., et al., "Regularization of the inverse Problem in Electrocardiography: A Model Study." Mathematical Biosciences, vol. 89, 1998, pp. 79-118.

Messnarz, B., et al., "A new spatiotemporal regularization approach for reconstruction of cardiac transmembrane potential patterns." IEEE transactions on Biomedical Engineering 51.2 (2004): 273-281.

Micchelli, C. A., et al., "Learning the kernel function via regularization." Journal of Machine Learning Research, vol. 6, 2005, pp. 1099-1125.

Myerburg R.J., et al., "Interpretation of outcomes of antiarrhythmic clinical trials: design features and population impact." Circulation. 1998;97:1514-21.

Narayan, S.M., et al., "Steep restitution of ventricular action potential duration and conduction slowing in human Brugada syndrome." Heart Rhythm. 2007;4:1087-9.

Nash, M.P., et al., "Evidence for multiple mechanisms in human ventricular fibrillation." Circulation 114.6 (2006): 536-542.

Naumova, V., et al. "A meta-learning approach to the regularized learning—case study: Blood glucose prediction." *Neural Networks*, vol. 33, 2012, pp. 181-193.

Naumova, V., et al. "Extrapolation in variable RKHSs with application to the blood glucose reading." *Inverse Problems*, vol. 27, No. 7, 2011, pp. 1-13.

O'Hanlon, R., et al., "Prognostic significance of myocardial fibrosis in hypertrophic cardiomyopathy." Journal of the American College of Cardiology. 2010;56:867-74.

Oster, H. S., et al., "The use of temporal information in the regularization of the inverse problem of electrocardiography." IEEE Transactions on Bio-Medical Engineering, vol. 39, No. 1, 1992, pp. 65-75.

Oster, H.S., et al., "Noninvasive electrocardiogramaging: reconstruction of epicardial potentials, electrograms, and isochrones and localization of single and multiple electrocardiac events." Circulation. 1997;96:1012-24.

Pfeifer, B., et al. "Patient-specific volume conductor modeling for non-invasive imaging of cardiac electrophysiology." *The Open Medical Informatics Journal*, vol. 2, 2008, pp. 32-41.

Ploux, S., et al. "Noninvasive electrocardiographic mapping to improve patient selection for cardiac resynchronization therapy: beyond QRS duration and left bundle branch block morphology." *Journal of the American College of Cardiology*, vol. 61, No. 24, 2013, pp. 2435-2443.

Ramanathan, C., et al. "Noninvasive electrocardiogramaging for cardiac electrophysiology and arrhythmia." *Nature Medicine*, vol. 10, No. 4, 2004, pp. 422-428.

Ramanathan, C., et al. "Noninvasive Electrocardiogramaging (ECGI): Application of the Generalized Minimal Residual (GMRes) Method." *Annals of Biomedical Engineering*, vol. 31, No. 8, 2003, pp. 981-994.

Rodriguez, L.-M., et al. "Variable patterns of septal activation in patients with left bundle branch block and heart failure." *Journal of Cardiovascular Electrophysiology*, vol. 14, No. 2, 2003, pp. 135-141.

Rotter, M., et al. "Reduction of fluoroscopy exposure and procedure duration during ablation of atrial fibrillation using a novel anatomical navigation system." *European Heart Journal*, vol. 26, No. 14, 2005, pp. 1415-1421.

(56) References Cited

OTHER PUBLICATIONS

Rudy, Y. "Noninvasive electrocardiogramaging of arrhythmogenic substrates in humans." Circulation Research, vol. 112, No. 5, 2013, pp. 863-874.
Schreck, D. M.,et. al. "Statistical methodology: VI. Mathematical modeling of the electrocardiogram using factor analysis." Academic Emergency Medicine, vol. 5, No. 9, 1998, pp. 929-934.
Singh, J. P., et al. "Left ventricular lead electrical delay predicts response to cardiac resynchronization therapy." Heart Rhythm, vol. 3, No. 11, 2006, pp. 1285-1292.
Stecker, E.C., et al., "Population-based analysis of sudden cardiac death with and without left ventricular systolic dysfunction: two-year findings from the Oregon Sudden Unexpected Death Study." J Am Coll Cardiol. 2006;47:1161-6.
Stevenson, W.G., et al., "Identification of reentry circuit sites during catheter mapping and radiofrequency ablation of ventricular tachycardia late after myocardial infarction." Circulation 1993;88:1647-70.
Sweeney, M. O., et al. "Analysis of ventricular activation using surface electrocardiography to predict left ventricular reverse volumetric remodeling during cardiac resynchronization therapy." Circulation, vol. 121, No. 5, 2010, pp. 626-634.
Taggart, P., et al. "Developing a novel comprehensive framework for the investigation of cellular and whole heart electrophysiology in the in situ human heart: Historical perspectives, current progress and future prospects."&nbsb;Progress in biophysics and molecular biology 115.2-3 (2014): 252-260.
Ten Tusscher, K. H. W. J., et al., "A model for human ventricular tissue." American Journal of Physiology—Heart and Circulatory Physiology 286.4 (2004): H1573-H1589.
Ten Tusscher, K.H.W.J., et al., "Alternans and spiral breakup in a human ventricular tissue model. American Journal of Physiology." Heart and Circulatory Physiology, vol. 291,2006, pp. H1088-H1100.
Tikhonov, A. N., et al. Solutions of ill-posed problems. Winston, (p. 258), 1997.
Tikhonov, A. N., et al., "Use of the regularization methods in non-linear problems." USSR Computational Mathematics and Mathematical Physics, vol. 5, 1965.
Tobon, C., et al., "Dominant frequency and organization index maps in a realistic three-dimensional computational model of atrial fibrillation." Europace 14.suppl 5 (2012): v25-v32.
Vadakkumpadan, F., et al. "Image-based estimation of ventricular fiber orientations for personalized modeling of cardiac electrophysiology." Medical Imaging, IEEE Transactions, vol. 31, No. 5, 2012, pp. 1051-1060.
Van der Graaf, A. W. M., et al. "Noninvasive imaging of cardiac excitation: current status and future perspective. Annals of Noninvasive Electrocardiology." The Official Journal of the International Society for Holter and Noninvasive Electrocardiology, Inc, vol. 19, No. 2, 2014, pp. 105-113.
Van Deursen, C. J., et al. "Vectorcardiography as a tool for easy optimization of cardiac resynchronization therapy in canine left bundle branch block hearts." Circulation: Arrhythmia and Electrophysiology, vol. 5, No. 3, 2012, pp. 544-552.
Vaquero, M., et al. "Cardiac Fibrillation: From Ion Channels to Rotors in the Human Heart." Heart Rhythm : The Official Journal of the Heart Rhythm Society, vol. 5, No. 6, 2008, pp. 872-879.
Varma, N., et al. "Electrocardiogramaging of patients with heart failure with left bundle branch block and response to cardiac resynchronization therapy." Journal of Electrocardiology, vol. 40,2007, pp. S174-S178.
Wang, Y., et al. "Noninvasive electroanatomic mapping of human ventricular arrhythmias with electrocardiographic imaging." Science Translational Medicine, vol. 3, No. 98, 2011, pp. 98ra84.
Wittkampf, F. H., et al. "LocaLisa new technique for real-time 3-dimensional localization of regular intracardiac electrodes." Circulation, vol. 99, No. 10, 1999, pp. 1312-1317.
Yamashita, Y. "Theoretical studies on the inverse problem in electrocardiography and the uniqueness of the solution." Biomedical Engineering, IEEE Transactions, vol. 11, 1982, pp. 719-725.
Yokokawa, M. et al., "Automated analysis of the 12-lead electrocardiogram to identify the exit site of prostinfarction ventricular tachycardia." Heart Rhythm Society vol. 9, No. 3, Mar. 2012: 330-334, (5 pages).
Yushkevich, P. A., et. al. "User-guided 3D active contour segmentation of anatomical structures: significantly improved efficiency and reliability." NeuroImage, vol. 31, No. 3, 2006, pp. 1116-1128.
Zhang, J., et al., "Cardiac electrophysiological substrate underlying the ECG phenotype and electrogram abnormalities in Brugada syndrome patients." Circulation. 2015;131:1950-9.
Zhang, X., et al. "Noninvasive three-dimensional electrocardiographic imaging of ventricular activation sequence." AJP-Heart Circulatory Physiology, vol. 289, 2005, pp. 2724-2732.
Man, S.-C et al.,"Reconstruction of standard 12-lead electrocardigrams from 12-lead electrocardiograms recorded with the Mason-Likar electrode configuration," Journal of Electrocardiology, vol. 14 (2008), pp. 211-219.
Extended European Search Report issued in European Application No. 19831553.3-1113, mailed Mar. 3, 2022, 9 pages.

* cited by examiner

Fig. 1

- Patients classified as responders/non-responders based on changes in cardiac function 3-6 months after CRT procedure measured using echocardiography
    - >10% reduction in end-systolic volume
    - >5% absolute change in ejection fraction

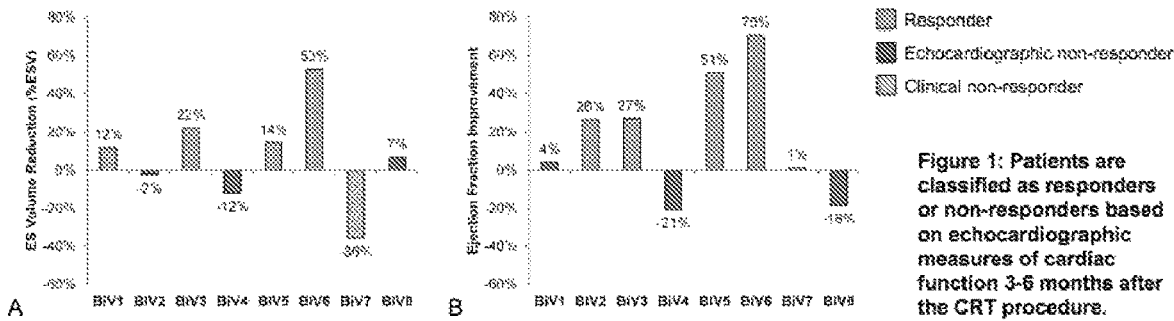

Figure 1: Patients are classified as responders or non-responders based on echocardiographic measures of cardiac function 3-6 months after the CRT procedure.

Fig. 2

* Baseline measures of mechanical and electrical function do not correlate well with functional improvement after CRT procedure

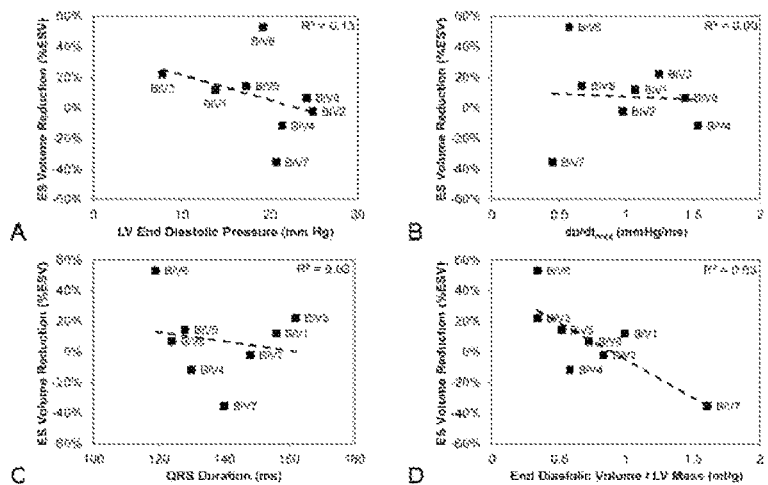

Figure 2: Measures of LV mechanical function such as end-diastolic pressure (A) and the maximum dp/dt (B) do not correlate with end-systolic volume reduction after CRT. The QRS duration (C) and the echocardiographic measure of dilatation (D) also do not correlate with functional improvement after CRT.

Figure 3: Different components of the patient-specific electromechanics model utilized in its construction.

Figure 4: CT image slices (A) were segmented and the resulting data points are used to fit the surfaces of the geometric biventricular model (B). Patient-specific hexahedral finite element mesh (C) is constructed from the surfaces for different patients (D).

Figure 5: Reconstructed diffusion tensors in the explanted donor heart (A) fitted to the geometric model (B).

Scar Region

Figure 6: The voxel intensities of the MIBI scan were reconstructed in 3D space and aligned to the anatomical model; a scalar field was fitted to define the region of the scar.

Figure 7: Electroanatomic activation time data (A) projected onto the LV surface of the finite element mesh and rendered as a field (B). Output of an electrophysiology simulation to generate myocardial activation times.

Figure 8: Simulated and Measured LV and RV Pressure and PV Loops.

Figure 9: Radial displacement between end-diastole and end-systole from the measured and simulated geometries.

Fig. 10
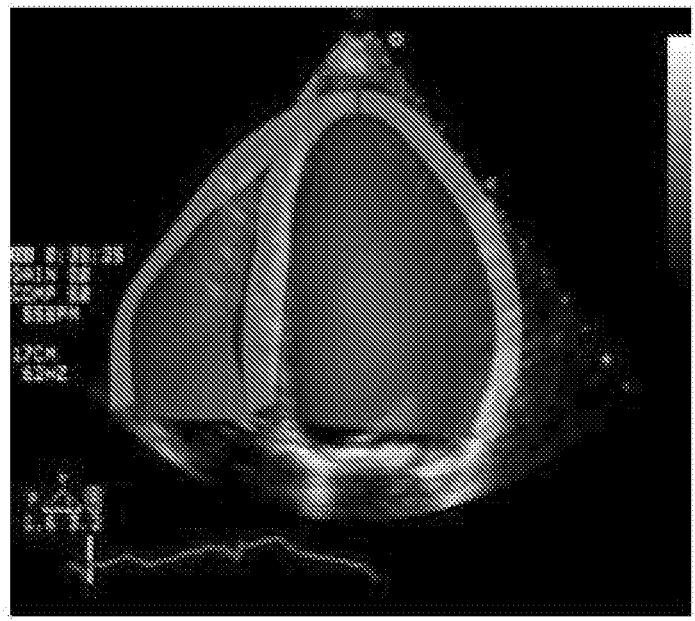
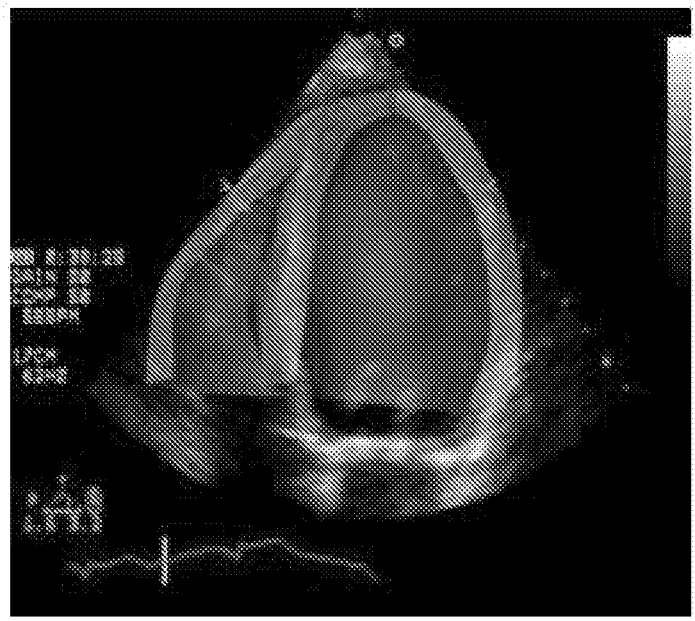
Figure 10: Comparison of ventricular geometry of the simulated heart (brown), overlaid on the clinical echocardiographic images of the same heart at end-diastole and end-systole.

Regional Stress-Strain Work Loops

Figure 11: Stress-strain loops used to compute the regional work density in a heart failure patient. The septal region performs minimal or negative work in patients who responded better to CRT.

Figure 12: Mean external work density and LV fraction performing negative work can be used to classify echocardiographic responders.

Classification of Echocardiographic Response

Figure 13: Receiver-operator characteristic (ROC) curves for using negative LV and septal work as classifiers of echocardiographic response to CRT. Echocardiographic response is classified using 10% reduction in end-systolic volume (A) or 5% absolute increase in ejection fraction (B).

Figure 14: Both coefficient of variation of external work density (A) and fraction of LV performing negative work (B) predict quantitative measures of left-ventricular reverse remodeling.

COMPOSITIONS, DEVICES AND METHODS FOR DIAGNOSING HEART FAILURE AND FOR PATIENT-SPECIFIC MODELING TO PREDICT OUTCOMES OF CARDIAC RESYNCHRONIZATION THERAPY

RELATED APPLICATIONS

This application is a national-phase entry of Patent Cooperation Treaty Application No. PCT/US2014/065841, filed Nov. 14, 2014, which claims the benefit of priority to U.S. Provisional Patent Application Serial No. (USSN) 61/905,138, filed Nov. 15, 2013. The aforementioned is applications are expressly incorporated herein by reference in their entirety and for all purposes.

STATEMENT AS TO FEDERALLY SPONSORED RESEARCH

This invention was made with government support under Grant No. HL096544, awarded by the National Institutes of Health (NIH), DHHS. The government has certain rights in this invention.

TECHNICAL FIELD

This invention generally relates to diagnostics, medical devices and therapies used in dyssynchronous heart failure (DHF), including cardiac resynchronization therapy (CRT) and use of biventricular pacemakers (BVPs). In particular, in alternative embodiments, provided are compositions, diagnostic techniques, medical devices or products of manufacture, systems, and methods for diagnosing the severity of DHF, predicting the response of patients with DHF to therapy including CRT, improving the response to therapy by informing the choice of therapeutic parameters such as CRT pacing lead locations or ventriculo-ventricular (VV) delays, or comprising: computing, measuring or determining the distributions of regional myocardial work and deriving from these measures of work heterogeneity. The work heterogeneity can be computed, measured or assessed using alternative measures derived from these distributions including but not limited to, the coefficient of variation of regional work (COVW), the mass or volume fraction of the whole heart, left ventricular (LV) wall, right ventricular (RV) wall or septal wall in which regional work is less than or equal to zero (MNW).

BACKGROUND

Cardiac resynchronization therapy (CRT) is a treatment for dyssynchronous heart failure (DHF) in which a pacemaker system can pace the heart in a manner intended to improve the synchrony of electrical activation of the heart walls. By pacing in one, two or more locations, pacemaker therapy can resynchronize a heart whose walls do not contract in synchrony, which occurs in approximately 25 to 50% of heart failure patients. By adjusting the timing of pacemaker stimuli, the improvement of mechanical function in the heart can be altered and optimized.

Different indices of dyssynchrony are found from echocardiography, electrocardiography, cardiac catheterization, or cardiac imaging to classify responders and non-responders to CRT. However, these metrics have shown neither high specificity and sensitivity nor good correlations with patient outcomes.

Previous studies based on data from experimental animals suggest that electrical dyssynchrony produces increased heterogeneity in regional myocardial work density, and model studies suggest that it could is a sensitive indicator of the mechanical deficit caused by electrical dyssynchrony. In a computational model of canine DHF, it was shown that the coefficient of variation (std. dev./mean) of the external work density (COVW) correlated well with measures of mechanical dyssynchrony. This metric was sensitive to the interaction effect between dilatation and electrical dyssynchrony that made mechanical dyssynchrony worse.

SUMMARY

In alternative embodiments, provided are compositions and methods for the clinical use of patient-specific computational models constructed from clinical data measured in patients clinically diagnosed with dyssynchronous heart failure (DHF) where the reduction of cardiac output or pumping performance occurs as a result of discoordinated ventricular contraction and may be exacerbated by valve regurgitation. This invention for the first time found that patients having more heterogeneous regional work distributions are more able to benefit from therapy intended to decrease dyssynchrony, and that the greatest responses to therapy can be achieved by the greatest reductions in the magnitude of work heterogeneity. In alternative embodiments, these computations or measurements are made before therapy based on measurements obtained before therapy to assess the severity of dyssynchronous heart failure or to determine the likelihood of a patient to respond to a therapy. In alternative embodiments, computations or determinations made before therapy can include computational simulations of possible therapeutic interventions such as cardiac resynchronization therapy (CRT) using different possible therapeutic parameters such as alternative pacing lead locations or VV pacing delay times. In alternative embodiments, the results of such computations or predictions of regional myocardial work distributions are used to select or advise the choice or therapeutic parameters intended to achieve best possible clinic responses or therapeutics outcomes. In alternative embodiments, these computations, predictions, measurements and/or determinations of regional myocardial work distributions are used after therapy to assess the response to treatment.

In alternative embodiments, provided are diagnostic tools or methods, including computer implemented methods, for:
predicting and optimizing the response of patients with dyssynchronous heart failure (DHF) to cardiac resynchronization therapy (CRT), and/or
for diagnosing dyssynchronous heart failure or the degree of dyssynchrony in dyssynchronous heart failure, comprising:
measuring or determining indices derived from the regional distribution of myocardial external work density (RDMW) prior to treatment as a diagnostic assessment of the severity of dyssynchronous heart failure or the adverse impact of dyssynchrony
on ventricular mechanical performance,
wherein optionally the indices measured or determined are selected from the group consisting of:
(i) the fraction of ventricular wall mass or volume, or a part thereof, optionally left ventricle (LV), right ventricle (RV), or septum, performing negative work (myocardial negative work density fraction, or MNWF), optionally having work done on it by the surrounding heart wall, (ii) regions of the left ventricular wall mass performing negative work (LVNW),
(iii) the coefficient of variation of external work density (COVW) or other measures of work dispersion or heterogeneity, optionally to predict amount of electromechanical dyssynchrony or the likely improvement in CRT response,
(iv) the fraction of the septal wall performing negative work (change in STNW or ΔSTNW), wherein a decrease in the fraction of the septal wall performing negative work (ΔSTNW) computed after simulated CRT is a predictor of pump function improvement and CRT response, and
(v) a combination thereof, and optionally predicting the potential response of patients with dyssynchronous heart failure (DHF) to cardiac resynchronization therapy (CRT), optionally predicting a reduction in end-systolic ventricular volume due to CRT, by using the myocardial negative work density fraction, or MNWF, or coefficient of variation (standard deviation divided by mean) of regional work density COVW or other measures of the heterogeneity or dispersion of RDMW, with greater values of heterogeneity corresponding to greater potential benefit of therapies that act to decrease dyssynchrony, and optionally the diagnostic tool or method is a computer implemented method, and optionally a value for COVW prior to therapy ranging from between about 1.0 to 1.25, indicates a low electromechanical dyssynchrony and predicts a weak CRT response, and optionally values in the range of between about 1.25 to 1.50 indicate a moderate electromechanical dyssynchrony and predicts a moderate CRT response, and optionally a value for COVW exceeding about 1.5 indicates a high mechanical dyssynchrony and predicts a strong CRT response, and optionally regions of the left ventricular wall mass performing negative work (LVNW) before therapy indicate an electromechanical dyssynchrony, and larger regions indicate more severe dyssynchrony and greater potential for benefit of CRT, and optionally values for LVNW below about 0.15 indicate low mechanical dyssynchrony and predict a weak CRT response, and optionally values for LVNW from between about 0.15 to 0.20 indicate moderate electromechanical dyssynchrony and predict a moderate CRT response, and optionally values for LVNW exceeding about 0.20 indicate a high electromechanical mechanical dyssynchrony and predict a strong CRT response, and optionally metrics for work heterogeneity can be used as a decision tool for choosing the correct intervention techniques for patients with DHF, where patients having high work heterogeneity, optionally COVW>1.5 LVNW>0.20 STNW>0.25 at baseline are ideal candidates for CRT, and optionally CRT may not be effective in patients with low baseline work heterogeneity, optionally COVW<1.25, LVNW<0.15 STNW<0.15, and optionally values for ΔSTNW ranging from between about 0 to 0.06 predict a low improvement and therefore a weak CRT response, and optionally ΔSTNW values from between about 0.06 to 0.12 indicate a moderate improvement and predict a moderate CRT response, and optionally ΔSTNW value reductions of between about 0.12-0.18 indicate a high improvement and predict a strong CRT response.

Any of these indices can be used as addition information aiding the clinical decision for the intervention technique. Based on the diagnostic embodiment, this exemplary method, or model, of the invention can aid in the decision as to whether or not a candidate would likely benefit from undergoing an ICD implantation procedure to apply CRT. Optimal CRT settings would reduce these quantities as closely as possible to zero.

In alternative embodiments, methods of the invention for computing the decrease in measures of the heterogeneity of regional work density can predict optimal therapeutic settings such as pacing lead locations and ventricle-to-ventricle (VV) delay times by simulating various settings and finding those settings that reduce the COVW, LVNW, STNW or other measures of the heterogeneity of RDMW to minimum values.

In alternative embodiments, provided are diagnostic tools or methods, including computer implemented methods, for predicting and/or optimizing the response of patients with dyssynchronous heart failure (DHF) to cardiac resynchronization therapy (CRT), comprising:

(a) measuring or determining indices derived from the regional distribution of myocardial external work density (RDMW) prior to treatment, wherein optionally the indices measured or determined are selected from the group consisting of:
(i) the fraction of ventricular wall mass or volume, or a part thereof, optionally left ventricle (LV), right ventricle (RV), or septum, performing negative work (myocardial negative work density fraction, or MNWF), optionally having work done on it by the surrounding heart wall,
(ii) regions of the left ventricular wall mass performing negative work (LVNW),
(iii) the coefficient of variation of external work density (COVW) or other measures of work dispersion or heterogeneity, optionally to predict amount of electromechanical dyssynchrony or the likely improvement in CRT response,
(iv) the fraction of the septal wall performing negative work (change in STNW or ΔSTNW), wherein a decrease in the fraction of the septal wall performing negative work (ΔSTNW) computed after simulated CRT is a predictor of pump function improvement and CRT response, and
(v) a combination thereof,
and
(b) computing the change in these indices of work heterogeneity following the simulated application of CRT in a computational model, wherein optionally change in these indices of work heterogeneity comprise:
(i) a decrease in the fraction of myocardium (or LV, RV, or septal myocardium) performing negative work (MNWF) of about 0.1 or greater; or
(ii) a decrease in the coefficient of variation of external work density (COVW) of about 0.5 or greater, wherein optionally a computed decrease in the fraction of the septum performing negative work correlates strongly with a positive response to therapy and an observed reduction in end-systolic volume, optionally approximately 3 to 6 months after CRT, wherein this correlation is based on the fact that higher values of the change correlate (with a correlation coefficient $r^2$ greater than 0.7) with better reductions in end-systolic relations; and lower values imply or predict less improvement, and these relations also show that a decrease of greater than 0.6 predicts a significant clinical improvement, and optionally a value for COVW prior to therapy ranging from between about 1.0 to 1.25, indicates a low electromechanical dyssynchrony and predicts a weak CRT response, and optionally values in the range of between about 1.25 to 1.50 indicate a moderate electromechanical dyssynchrony and predicts a moderate CRT response, and optionally a value for COVW exceeding about 1.5 indicates a high mechanical dyssynchrony and predicts a strong CRT response, and optionally regions of the left ventricular wall mass performing negative work (LVNW) before therapy indicate an electromechanical dyssynchrony, and larger regions indicate more severe dyssynchrony and greater potential for benefit of CRT, and optionally values for LVNW below about 0.15 indicate low mechanical dyssynchrony and predict a weak CRT response, and optionally values for LVNW from between about 0.15 to 0.20 indicate moderate electromechanical dyssynchrony and predict a moderate CRT response, and optionally values for LVNW exceeding about 0.20 indicate a high electromechanical mechanical dyssynchrony and predict a strong CRT response, and optionally metrics for work heterogeneity can be used as a decision tool for choosing the correct intervention techniques for patients with DHF, where patients having high work heterogeneity (optionally COVW>1.5, LVNW>0.20 SNW>0.25 at baseline are ideal candidates for CRT, and optionally CRT may not be effective in patients with low baseline work heterogeneity (optionally COVW<1.25, LVNW<0.15, STNW<0.15, and optionally values for ΔSTNW ranging from between about 0 to 0.06 predict a low improvement and therefore a weak CRT response, and optionally ΔSTNW values from between about 0.06 to 0.12 indicate a moderate improvement and predict a moderate CRT response, and optionally ΔSTNW value reductions of between about 0.12-0.18 indicate a high improvement and predict a strong CRT response.

An optimization protocol seeks pacing conditions including pacing lead locations and/or VV delays that reduce the magnitude of one or any combination of the measures of regional heterogeneity of myocardial work density to as close as possible to zero.

In alternative embodiments, provided are diagnostic tools or methods, including computer implemented methods, for improving and/or optimizing the response of patients with dyssynchronous heart failure (DHF) to cardiac resynchronization therapy (CRT), comprising:

(a) measuring or determining indices derived from the regional distribution of myocardial external work density (RDMW) prior to treatment, wherein optionally the indices measured or determined are selected from the group consisting of:
(i) the fraction of ventricular myocardium, or a part thereof, optionally left ventricle (LV), right ventricle (RV), or septum, performing negative work (myocardial negative work density fraction, or MNWF), optionally having work done on it by the surrounding heart wall, (ii) the coefficient of variation of external work density (COVW) or other measures of work dispersion or heterogeneity, optionally comprising the standard deviation, quartiles or extrema of the regional work distributions, (iii) and a combination thereof, and (b) computing the change in these indices of work heterogeneity under varied therapeutic conditions, optionally comprising varied pacing lead locations and varied VV delay times between stimulation of left and right ventricular pacing electrodes, wherein optionally:
(i) a decrease of at least 0.06 for STNW and/or 0.1 for LVNW in the fraction of myocardium (or LV, RV, or septal myocardium) performing negative work (MNWF) in response to various numbers and locations of pacing leads or various different delay times between stimulation of different pacing allows assessment of which therapeutic parameters (e.g., what numbers and locations of pacing leads or what different delay times between stimulation of different pacing sites) will result in the greatest decrease in absolute MNWF; or (ii) a decrease of at least 0.5 in the coefficient of variation of external work density (COVW) in response to various numbers and locations of pacing leads or various different delay times between stimulation of different pacing allows assessment of which therapeutic parameters (e.g., what numbers and locations of pacing leads or what different delay times between stimulation of different pacing sites) will result in the greatest decrease in absolute COVW, wherein optionally the computed decrease in the fraction of the septum performing negative work correlates strongly, or $r^2 > 0.7$, with a positive response to therapy and observed reduction in end-systolic volume about 3 to 6 months after CRT, wherein optionally an alteration of pacing lead locations and delay times significantly effects the predicted decrease in work heterogeneity indices, and optionally, for an optimal response to therapy, vary the VV delay of the simulated CRT in the model until one or any combination of the indices COVW, LVNW or STNW is reduced to the lowest absolute value, realizing that as delays are varied too much the heart could be made dyssynchronous in the opposite direction, which would not be beneficial.

In alternative embodiments, provided are computer program products for processing data, the computer program product comprising: computer-executable logic or algorithms contained on (optionally embedded or non-transitory on) a computer-readable medium and configured for causing the following computer-executed step to occur: at least one method, or computer-implemented method, of the invention.

In alternative embodiments, provided are computer systems comprising a processor and a data storage device wherein said data storage device has stored thereon: a computer program product for implementing a computer-implemented method of the invention, wherein optionally the computer-executable logic or algorithms for executing the computer-implemented methods are embedded or are non-transitory on the computer system.

In alternative embodiments, provided are Graphical User Interface (GUI) computer program products comprising: a computer program product for implementing a computer-implemented method of the invention, wherein optionally the computer-executable logic or algorithms for executing the computer-implemented method are embedded or are non-transitory on the GUI computer program product.

In alternative embodiments, provided are computer systems comprising a processor and a data storage device wherein said data storage device has stored thereon: (a) a computer program product for implementing a computer-implemented method of the invention; (b) a computer program product for processing data generated by a method of the invention; (c) a Graphical User Interface (GUI) computer program product of the invention; or, (d) a combination thereof.

In alternative embodiments, provided are non-transitory memory media comprising program instructions for running, processing and/or implementing: (a) a computer program product for implementing a computer-implemented method of the invention; (b) a computer program product for processing data generated by a method of the invention; (c) a Graphical User Interface (GUI) computer program product of the invention; (d) a computer system of the invention, or (e) a combination thereof.

In alternative embodiments, provided are computer-readable storage media comprising a set of or a plurality of computer-readable instructions that, when executed by a processor of a computing device, cause the computing device to run, process and/or implement: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention, or (f) a combination thereof.

In alternative embodiments, provided are computer program products comprising: a computer-readable storage medium; and program instructions residing in said storage medium which, when executed by a computer, run, process and/or implement: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention, or (g) a combination thereof.

In alternative embodiments, provided are computer program storage devices, embodied on a tangible computer readable medium, comprising: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; or (h) a combination thereof.

In alternative embodiments, provided are computer or equivalent electronic systems, comprising: a memory; and a processor operatively coupled to the memory, the processor adapted to execute program code stored in the memory to: run, process and/or implement: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; (h) a computer program storage device of the invention; or (i) a combination thereof.

In alternative embodiments, provided are products of manufacture, medical devices, pacemakers, or biventricular pacemakers, comprising, or having embedded or non-transiently contained therein: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; (h) a computer program storage device of the invention; or (i) a combination thereof.

In alternative embodiments, the products of manufacture, medical devices, pacemakers or biventricular pacemakers of the invention are manufactured or configured as a programmable implantable cardioverter-defibrillator (ICD) or CRT-D including a defibrillator in case defibrillation is needed, an implantable defibrillator, a dual-chamber defibrillator or a single-chamber defibrillator, or a CRT-P where there is no defibrillator but the CRT-P has a pacing system alone without the defibrillator.

In alternative embodiments, the products of manufacture, medical devices, pacemakers or biventricular pacemakers of the invention further comprises a computer, or a minicomputer, or circuitry comprising or have embedded or intransiently configured therein: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; (h) a computer program storage device of the invention; or (i) a combination thereof.

In alternative embodiments, provided are products of manufacture, medical devices, pacemakers or biventricular pacemakers manufactured or configured as comprising a remote communication device for remotely and operably interacting with: (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; (h) a computer program storage device of the invention; or (i) a combination thereof, wherein optionally the remote communication is by internet or telephone. In alternative embodiments, the products of manufacture, medical devices, pacemakers or biventricular pacemakers are manufactured or configured as a programmable implantable cardioverter-defibrillator (ICD) or CRT-D including a defibrillator in case defibrillation is needed, an implantable defibrillator, a dual-chamber defibrillator or a single-chamber defibrillator, or a CRT-P where there is no defibrillator but the CRT-P has a pacing system alone without the defibrillator.

In alternative embodiments, provided are systems or methods comprising:

(1) a product of manufacture, medical device, or biventricular pacemaker, and (2) (a) a computer program product for implementing a computer-implemented method of the invention; (b) a computer program product for processing data generated by a method of the invention; (c) a Graphical User Interface (GUI) computer program product of the invention; (d) a computer system of the invention, (e) a non-transitory memory medium of the invention; (f) a computer-readable storage medium of the invention; (g) a computer program product of the invention; (h) a computer program storage device of the invention; or (i) a combination thereof, wherein the product of manufacture, medical device, or biventricular pacemaker is manufactured or configured as comprising a remote communication device for remotely operably interacting with any one or several elements of (2), wherein optionally the remote communication is by internet or telephone or equivalent electronic device.

In alternative embodiments, provided are compositions, medical devices or products of manufacture, systems and methods for predicting the response of patients with dyssynchronous heart failure to cardiac re-synchronization therapy (CRT), comprising: (a) measuring or determining the fraction of the LV/septum performing negative work (LVNW); and, (b) measuring or determining the coefficient of variation of external work density (COVW), wherein the LVNW fraction performing negative work and coefficient of variation COVW (sd/mean) correlated strongly with observed reduction in end-systolic volume after CRT.

In alternative embodiments, provided are computer-implemented methods for predicting the response of patients with dyssynchronous heart failure to cardiac re-synchronization therapy (CRT), comprising: (a) measuring or determining the fraction of the LV/septum performing negative work (LVNW); and (b) measuring or determining the coefficient of variation of external work density (COVW), wherein the LVNW fraction performing negative work and coefficient of variation COVW (sd/mean) correlated strongly with observed reduction in end-systolic volume after CRT.

In alternative embodiments, provided are computer program products for processing data, the computer program product comprising: computer-executable logic and/or algorithms contained on a computer-readable medium and configured for causing the following computer-executed step to occur: for executing the computer-implemented method of the invention.

In alternative embodiments, provided are computer systems comprising a processor and a data storage device wherein said data storage device has stored thereon: a computer program product for implementing a computer-implemented method of the invention.

In alternative embodiments, provided are products of manufacture, or a medical device, or a biventricular pacemaker, comprising elements for carrying out or executing the computer-implemented method of the invention, including embedded or non-transitory memory medium, or embedded or non-transitory computer program products, of the invention for executing the computer-implemented method.

In alternative embodiments, provided are uses of a product of manufacture, or a medical device, or a biventricular pacemaker for carrying out or executing the computer-implemented method of the invention.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 1 graphically illustrates data of: ES volume reduction as % ESV (FIG. 1A) and ejection fraction improvement (FIG. 1B), where patients are classified as responders or non-responders based on echocardiographic measures of cardiac function 3 to 6 months after a CRT procedure; as discussed in detail in Example 1, below.

FIG. 2 graphically illustrates measures of LV mechanical function: FIG. 2(A) measures ES volume reduction as % ESV as a function of LV end diastolic pressure; FIG. 2(B) measures ES volume reduction as % ESV as a function of $dp/dt_{max}$; FIG. 2(C) measures ES volume reduction as % ESV as a function of QRS duration; FIG. 2(D) measures ES volume reduction as % ESV as a function of end diastolic volume; as discussed in detail in Example 1, below.

FIG. 8 illustrates simulated and measured LV and RV pressure and PV loops, with FIG. 8A measuring pressure as a function of time; and FIG. 8B measuring pressure as a function of volume; and, FIG. 9 illustrates radial displacement between end-diastole and end-systole from the measured and simulated geometries, with FIG. 9A measuring (measured and simulated) radial displacement as a function of the left ventricular region; and FIG. 9B graphically and as a table displays the data of FIG. 9A; as discussed in detail in Example 1, below.

FIG. 10 schematically illustrates a comparison of ventricular geometry of the simulated heart overlaid on the clinical echocardiographic images of the same heart at end-diastole, as illustrated in FIG. 10(A), and end-systole, as illustrated in FIG. 10(B); as discussed in detail in Example 1, below.

FIG. 11(A) illustrates RV free wall stress-strain loops; FIG. 11(B) illustrates septum stress-strain loops; FIG. 11(C) illustrates anterior-posterior and LV free wall stress-strain loops; as discussed in detail in Example 1, below.

FIG. 12(B) graphically illustrates the measurement of LV fraction performing negative work in the same patient samples as FIG. 12(A); as discussed in detail in Example 1, below.

FIG. 13(B) graphically illustrates data measuring true positive rate and a function of false positive rate of negative LV work (at 0.84) and negative septal work (at 0.81); as discussed in detail in Example 1, below.

FIG. 14B measures ES volume reduction as a function of LV fraction performing negative work); as discussed in detail in Example 1, below.

Like reference symbols in the various drawings indicate like elements.

Figure 3:
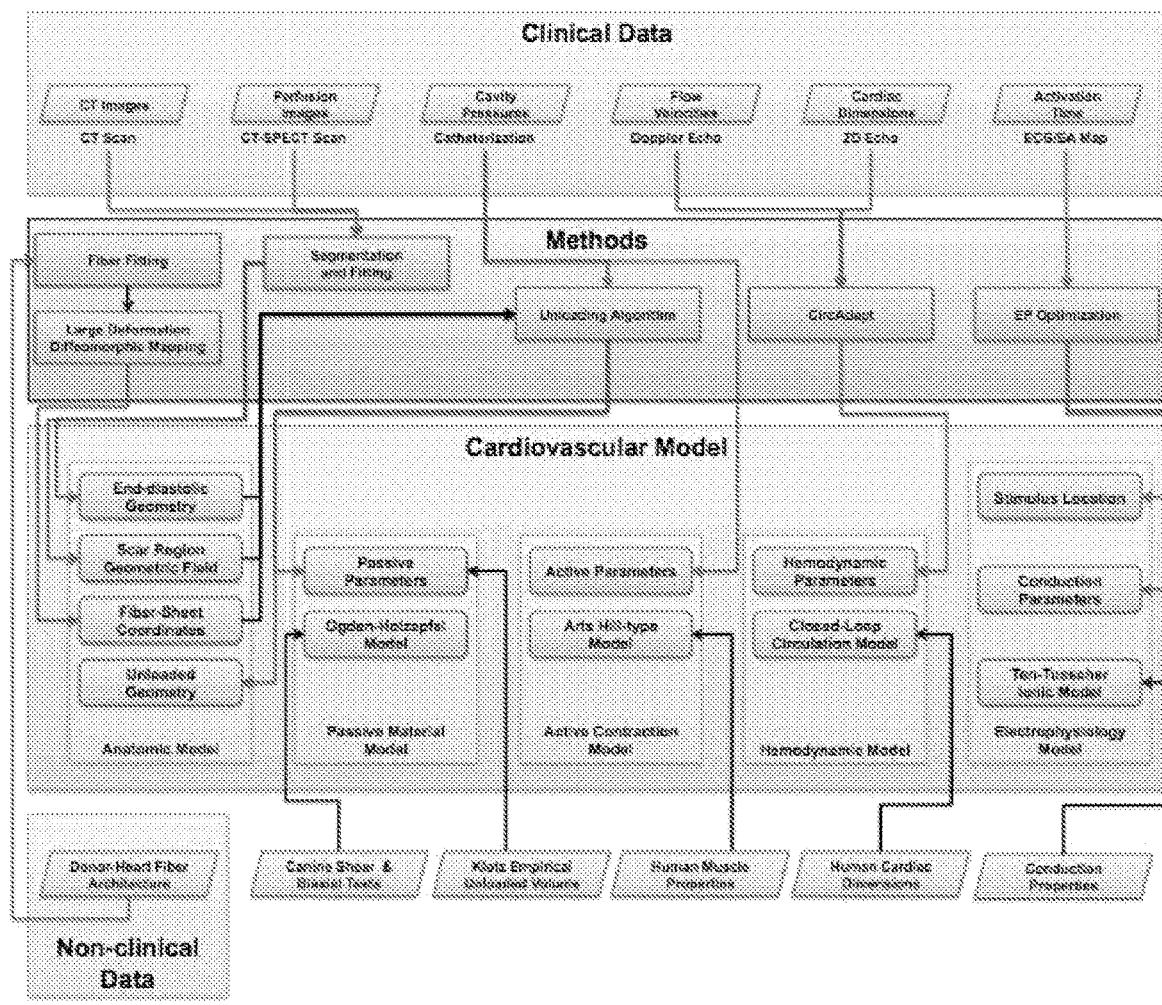
FIG. 3 schematically illustrates different components of an exemplary patient-specific electromechanics model, or method (including a computer-implemented method, of the invention; as discussed in detail in Example 1, below.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, provided are compositions, medical devices or products of manufacture, systems, diagnostic tools, and methods (including computer implemented methods) for assessing the severity of dyssynchronous heart failure, for identifying the clinical candidates best indicated for CRT or other therapy intended to reduce dyssynchrony, and for optimizing outcomes of therapy including by identifying most effective pacing protocols or electrode locations for a specific patient. In alternative embodiments, the compositions, medical devices or products of manufacture, systems and methods (including computer implemented methods) of the invention are used to assess the severity of or predict the response of patients with DHF to CRT by using a patient-specific computational model.

In alternative embodiments, the compositions, medical devices or products of manufacture, systems, diagnostic tools, and methods (including computer implemented methods) of the invention are used to predict the response of patients with DHF to CRT or other therapy using a patient-specific computational model to compute biomarkers by using indices derived from the regional distribution of myocardial external work density RDMW, for example, by using the fraction of the whole myocardium, the LV free wall or the septum performing negative work (MNW) or the coefficient of variation of external work density (COVW) using patient data obtained before therapy, or other properties of the regional distribution of myocardial work, stress, or strain or their changes as predicted by the computer model simulating CRT or pacemaker or other therapy.

In alternative embodiments, by using these biomarkers, methods of this invention can be significantly better than existing predictors of the response to CRT as measured by the reduction in end-systolic left ventricular volume three to six months after pacemaker implantation, and methods of this invention can more accurately discriminate clinical responders from non-responders. Since about 30% to 50% of CRT candidates are non-responders to therapy, the methods of the invention can identify best clinical candidates for CRT and help optimize outcomes of CRT by varying pacing protocols and electrode locations.

In alternative embodiments, provided are methods (including computer-implemented methods) for constructing patient-specific electromechanical finite-element models of the cardiovascular system, and methods for estimating their parameters from clinically available measurements made before the CRT procedure. In alternative embodiments, methods of the invention comprise:

Constructing patient-specific finite-element meshes from patient cardiac images;

Incorporating measurements of human ventricular myofiber architecture;

Estimating the cardiac electrical activation parameters using patient body surface or heart surface electrical recordings and using these for three-dimensional simulations of cardiac electrical activation patterns;

Estimating patient-specific resting myocardial material properties using hemodynamic and cardiac functional measurements by adjusting parameters of the resting myocardial constitutive model to achieve normalized pressure-volume relations consistent with human measurements, such as those described by Klotz et al., 2006, American Journal of Physiology-Heart and Circulatory Physiology, 291:H403-H12;

Computing patient-specific model of unloaded ventricular geometry using a dual or inverse method such as that described by Krishnamurthy et al., 2013 (2013) J. Comput. Physics 244:4-21;

Estimating or optimizing parameters of cardiac muscle contraction using patient-specific measurements of cardiac performance such as ventricular pressures and volume changes from cardiac catheterization, non-invasive blood pressure measurement, echocardiography or other clinical methods.

Estimating parameters of a close-loop model of the circulation using hemodynamic and cardiac functional measurements from cardiac catheterization, echocardiography, non-invasive blood pressure measurement or other methods together with an optimization or adaptation scheme, such as the CircAdapt model of the cardiovascular system, as described e.g., by Arts et al, American Journal of Physiology —Heart and Circulatory Physiology, 288 (4) (2005), p. H1943, and coupling the finite element biventricular model to circulation model using methods algorithms, e.g., such as those described by Kerckhoffs et al, (2007) Ann Biomed Eng 35:1-18;

Computing specific results derived from the cardiac model analysis of the patient before treatment that serve as diagnostic indicators of the functional severity of cardiac dyssynchrony or as predictive biomarkers of response to a therapy such as CRT.

These exemplary models of the invention have been validated by comparing the pressure time course from cardiac catheterization and regional displacements from echocardiography with patient-specific model computations.

In alternative embodiments, provided are compositions, medical devices or products of manufacture, systems, diagnostic tools, and methods (including computer-implemented methods) to generate the stress-strain values and loops at different regions of the left ventricle to compute the external work density of different regions in the myocardium. In alternative embodiments, using this distribution of fiber or myocardial work density, the fraction of the LV or the septum performing negative work, the COVW, or other measure of the distribution, is computed as a biomarker for the regional mechanical heterogeneity. This biomarker is then used to assess the severity of dyssynchrony, to classify whether a patient will be a responder or a non-responder, or to predict the improvement in ventricular function resulting from therapy. In addition, in alternative embodiments, the relative magnitude of this biomarker predicts the degree of left ventricular reverse remodeling as measured by end-systolic volume reduction.

In alternative embodiments, provided are compositions, medical devices or products of manufacture, systems, diagnostic tools, and methods (including computer-implemented methods) to simulate the CRT procedure to predict differential responses to different CRT pacing lead sites, as well as timing parameters and protocols.

Figure 13:
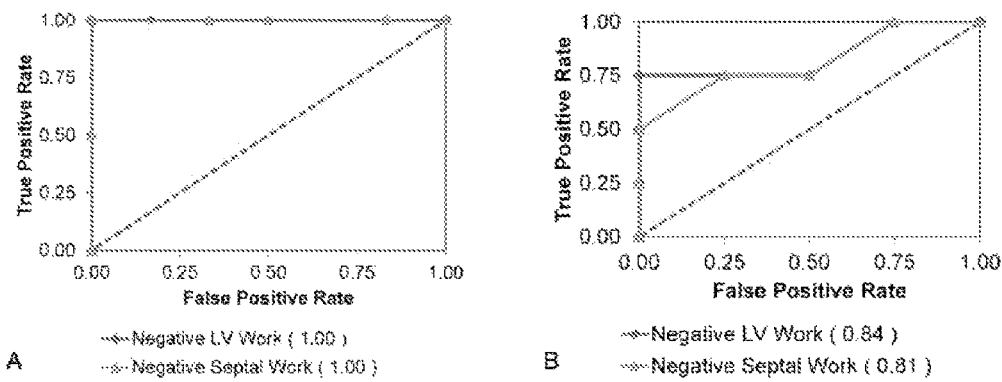
FIG. 13 illustrates receiver-operator characteristic (ROC) curves for using negative LV and septal work as classifiers of echocardiographic response to CRT; where FIG. 13(A) graphically illustrates data measuring true positive rate and a function of false positive rate of negative LV work (at 1.00) and negative septal work (at 1.00)
Figure 14:
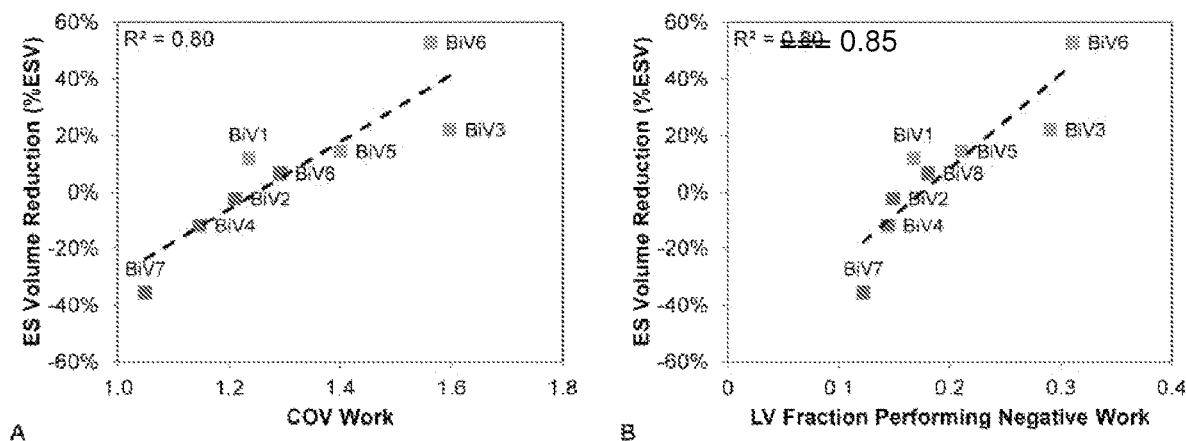
FIG. 14 graphically illustrates both coefficient of variation of external work density, as illustrated in FIG. 14(A), and fraction of LV performing negative work, as illustrated in FIG. 14(B); where FIG. 14(A) measures ES volume reduction as a function of COV work.
Figure 15:
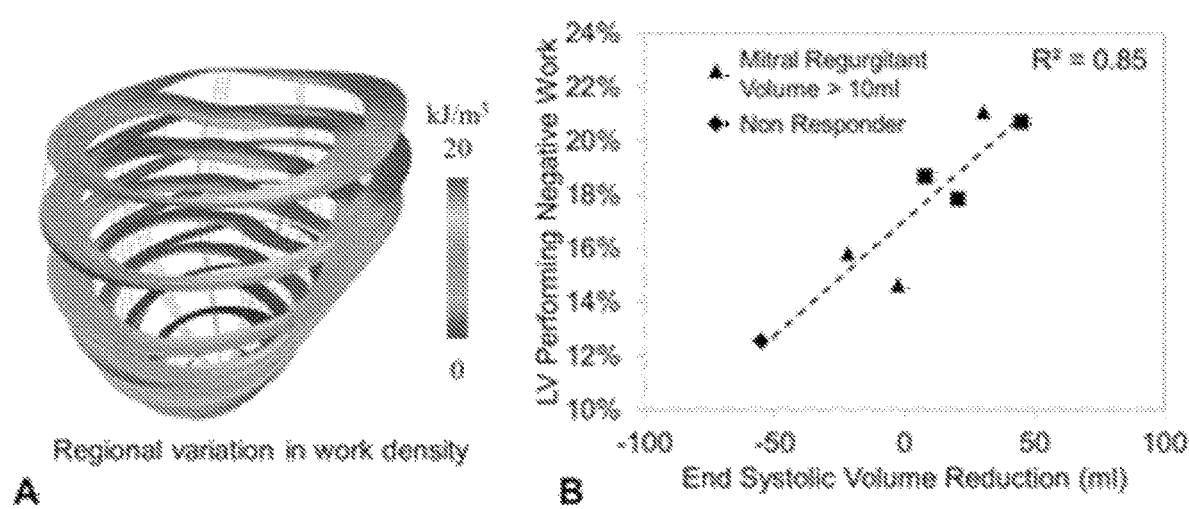
FIG. 15 illustrates results of using exemplary patient-specific (PS) computational models of the invention: as schematically illustrated in FIG. 15A, spatial distribution of myocardial work density was computed from baseline models; and as graphically illustrated in FIG. 15B, two measures of the distribution, LV fraction performing negative work and coefficient of variation (sd/mean) correlated strongly with observed reduction in end-systolic volume after CRT, respectively; as discussed in detail in Example 1, below.

The efficacy of the invention has been validated in eight patients with DHF. The work heterogeneity metrics were all able to discriminate the non-responders based on end-systolic volume reduction, as illustrated in FIG. 14. In addition, the area under the receiver-operator characteristic (ROC) curves for these metrics for identifying the responders from the non-responders using different echocardiographic measures of response were all greater than 0.8, as illustrated in FIG. 13.

In alternative embodiments, devices, appliances and products of manufacture of the invention, or any components thereof, are scaled to different proportional dimensions to accommodate the differing patients of all ages and physical dimensions. In alternative embodiments, devices, appliances and products of manufacture of the invention, or any components thereof, can be designed to have optimum dimensional relationships, to include variations in size, materials, shape, form, function and manner of operation, assembly and use, as are deemed readily apparent to one skilled in the art, and all equivalent relationships to those illustrated in the drawings and described in the specification are intended to be encompassed by the present inventive subject matter.

Computer Systems and Data Storage Devices

In alternative embodiments, computer-implemented methods of the invention, in whole or in part, will implement, or require the implementation of, using a machine, a computer, a computer system or equivalents, within which a set of instructions for causing the computer, computer system or machine to perform any one or more of the protocols or methodologies of the invention may be executed. In alternative embodiments, the machine may be connected (e.g., networked) to other machines, e.g., in a Local Area Network (LAN), an intranet, an extranet, or the Internet, or any equivalents thereof. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. The term "machine" shall also be taken to include any collection of machines, computers or products of manufacture that individually or jointly execute a set (or multiple sets) of instructions to perform any one or more of the methodologies of the invention.

In alternative embodiments, an exemplary computer system of the invention comprises a processing device (processor), a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a data storage device, which communicate with each other via a bus.

In alternative embodiments, a processor represents one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. In alternative embodiments the processor is configured to execute the instructions (e.g., processing logic) for performing the operations and steps discussed herein.

In alternative embodiments the computer system further comprises a network interface device. The computer system also may include a video display unit (e.g., a liquid crystal display (LCD) or a cathode ray tube (CRT)), an alphanumeric input device (e.g., a keyboard), a cursor control device (e.g., a mouse), and a signal generation device (e.g., a speaker).

In alternative embodiments, the data storage device (e.g., drive unit) comprises a computer-readable storage medium on which is stored one or more sets of instructions (e.g., software) embodying any one or more of the protocols, methodologies or functions of this invention. The instructions may also reside, completely or at least partially, within the main memory and/or within the processor during execution thereof by the computer system, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies of the present invention. In alternative embodiments the term "machine-accessible storage medium" shall accordingly be taken to include, but not be limited to, solid-state memories, and optical and magnetic media.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The following examples, and the figures, are intended to clarify the invention, and to demonstrate and further illustrate certain preferred embodiments and aspects without restricting the subject of the invention to the examples and figures.

EXAMPLES

Example 1

Exemplary Methods and Products of Manufacture

The following example describes exemplary methods and devices of the invention.

Figure 11:
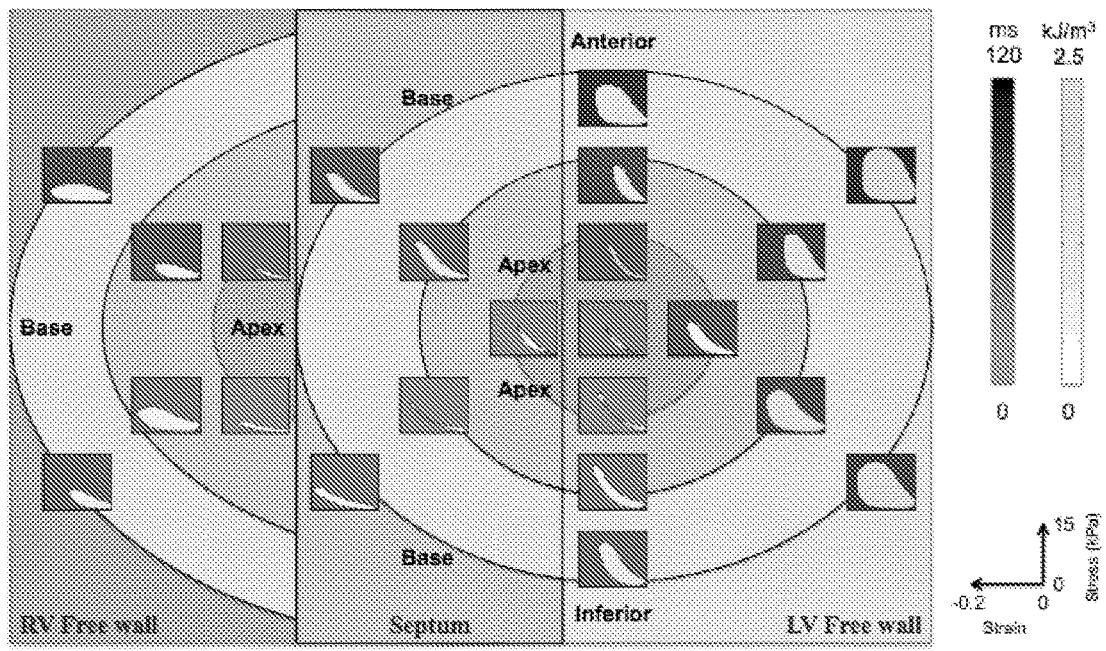
FIG. 11 schematically illustrates stress-strain loops used to compute regional work density; the schematic demonstrates that the septal region performs minimal or negative work in patients who responded better to CRT.

We developed patient-specific (PS) computational models of 8 male patients aged >60 years with NYHA class III heart failure, ejection fraction <33%, left bundle branch block with QRS duration >120 ms, mitral regurgitation >10 ml (in 3 patients), and myocardial infarction (in 5 patients). Bi-ventricular geometry segmented from end-diastolic cardiac CT images, hemodynamic measurements from cardiac catheterization, electrophysiological measurements from ECG and electroanatomic mapping were used to construct detailed PS finite-element models of ventricular electromechanics coupled to a closed-loop circulation model. Spatial distribution of myocardial work density computed from baseline models (as illustrated in FIG. 11) varied significantly between patients (mean 0.7-5.3, sd 1.0-6.5 kJ/m$^3$). Two measures of the distribution, LV fraction performing negative work and coefficient of variation (sd/mean) correlated strongly with observed reduction in end-systolic volume after CRT ($R^2$=0.85, 0.80 respectively; as illustrated in FIG. 14). Clinical indices based on model-computed strains such as internal stretch fraction (ISF) and circumferential uniformity ratio estimate (CURE) as well as the measured QRS duration did not correlate as well (ISF 0.15; CURE 0.23; QRS 0.22) possibly due to infarction.

In conclusion, functional improvement following CRT is greatest in patients with the largest region of LV performing negative work before treatment.

Echocardiographic Response

Patients classified as responders/non-responders based on changes in cardiac function 3-6 months after CRT procedure measured using echocardiography: >10% reduction in end-systolic volume; >5% absolute change in ejection fraction.

FIG. 1 graphically illustrates data of: ES volume reduction as % ESV (FIG. 1A) and ejection fraction improvement (FIG. 1B), where patients are classified as responders or non-responders based on echocardiographic measures of cardiac function 3 to 6 months after the CRT procedure. Baseline measures of mechanical and electrical function do not correlate well with functional improvement after CRT procedure.

FIG. 2 graphically illustrates measures of LV mechanical function, such as: end-diastolic pressure, as illustrated in FIG. 2(A), and the maximum rate of change of left ventricular pressure (dp/dt), as illustrated in FIG. 2(B), do not correlate with end-systolic volume reduction after CRT. The QRS duration, as illustrated in FIG. 2(C), and the echocardiographic measure of dilatation, as illustrated in FIG. 2(D), also do not correlate with functional improvement after CRT.

Construction of Comprehensive Patient-Specific Model

FIG. 3 illustrates different components of an exemplary patient-specific electromechanics model, or method (including a computer-implemented method, of the invention, including use of clinical data, a cardiovascular model and non-clinical data.

Bi-Ventricular Geometry

Figure 4:
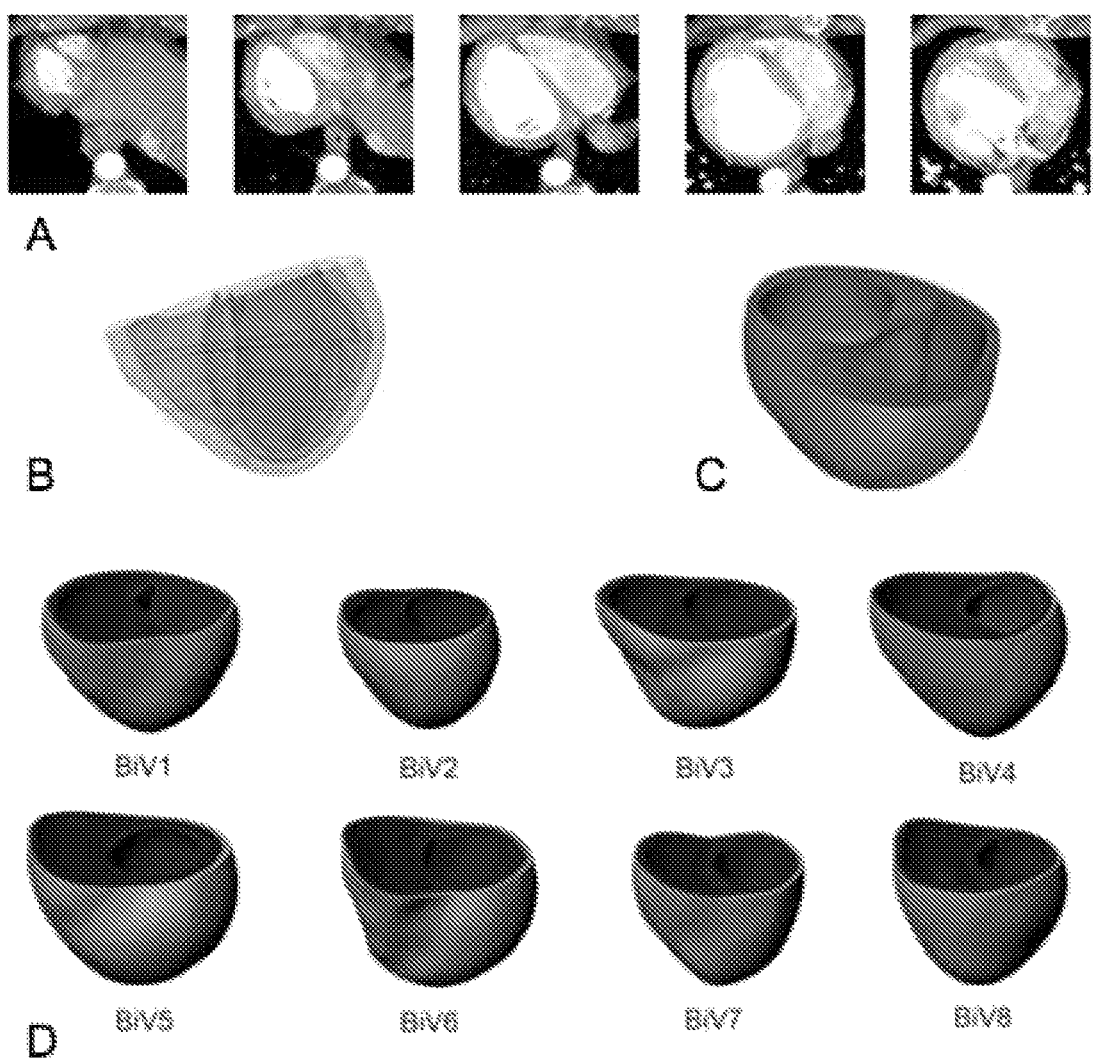
FIG. 4 schematically illustrates: images of CT image slices FIG. 4(A) that were segmented and the resulting data points are used to fit the surfaces of the geometric ventricular model, as illustrated in FIG. 4(B); and patient-specific hexahedral finite element mesh, as illustrated in FIG. 4(C), is constructed from the surfaces for different patients, as illustrated in FIG. 4(D); as discussed in detail in Example 1, below.

FIG. 4 illustrates images of CT image slices FIG. 4(A) that were segmented and the resulting data points are used to fit the surfaces of the geometric ventricular model, as illustrated in FIG. 4(B). Patient-specific hexahedral finite element mesh, as illustrated in FIG. 4(C), is constructed from the surfaces for different patients, as illustrated in FIG. 4(D).

Myofiber Architecture

Figure 5:
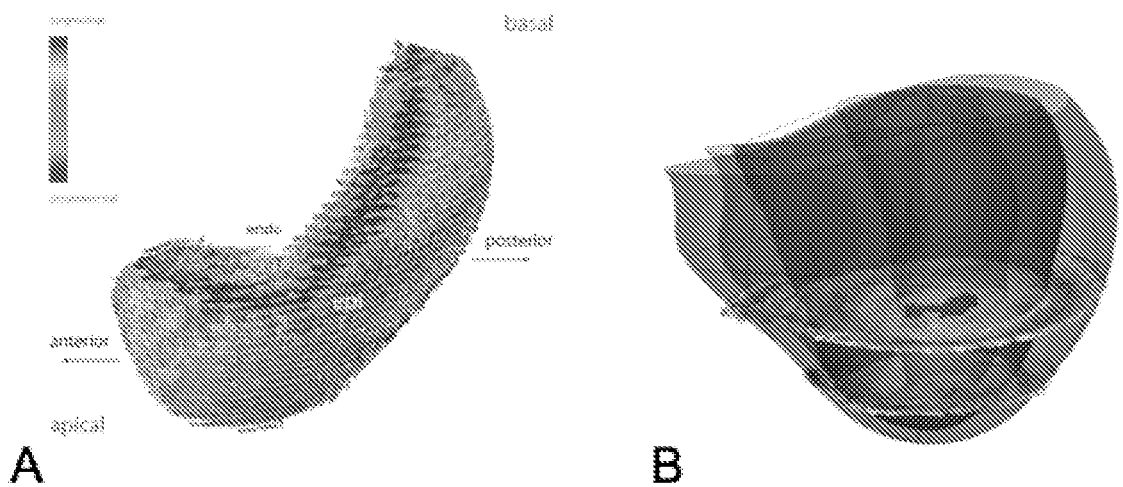
FIG. 5 schematically illustrates reconstructed diffusion tensors in the explanted donor heart, as illustrated in FIG. 5(A), fitted to the geometric model, as illustrated in FIG. 5(B); as discussed in detail in Example 1, below.

FIG. 5 illustrates reconstructed diffusion tensors in the explanted donor heart, as illustrated in FIG. 5(A), fitted to the geometric model, as illustrated in FIG. 5(B).

Scar Region

Figure 6:
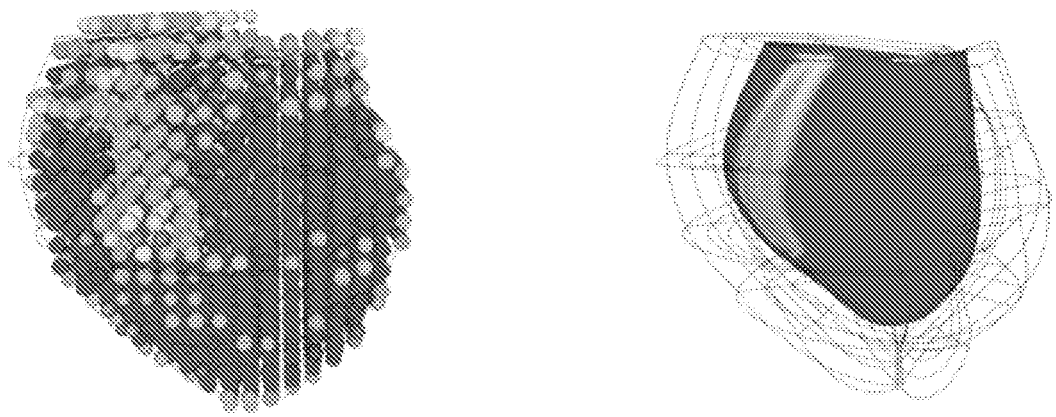
FIG. 6 schematically illustrates how the voxel intensities of the MIBI scan were reconstructed in 3D space, as illustrated in FIG. 6(A), and aligned to the anatomical model, as illustrated in FIG. 6(B); as discussed in detail in Example 1, below.

FIG. 6 illustrates how the voxel intensities of the MIBI (methoxy-isobutyl-isonitrile) scan were reconstructed in 3D space, as illustrated in FIG. 6(A), and aligned to the anatomical model, as illustrated in FIG. 6(B); a scalar field was fitted to define the region of the scar.

Activation Time

Figure 7:
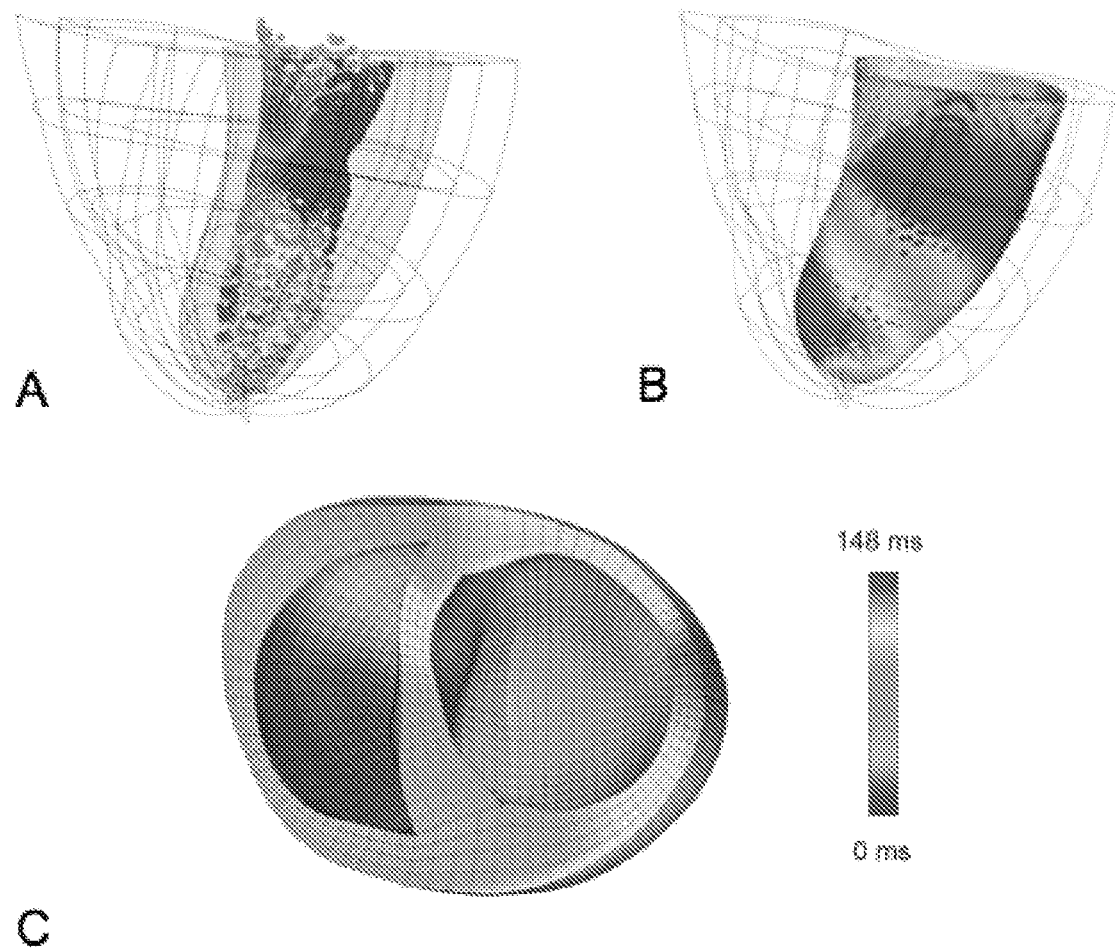
FIG. 7 schematically illustrates electroanatomic activation time data, as illustrated in FIG. 7(A), projected onto the LV surface of the finite element mesh and rendered as a field, as illustrated in FIG. 7(B), and aligned to an anatomical model, as illustrated in FIG. 7(C); as discussed in detail in Example 1, below.

FIG. 7 illustrates electroanatomic activation time data, as illustrated in FIG. 7(A), projected onto the LV surface of the finite element mesh and rendered as a field, as illustrated in FIG. 7(B), and aligned to an anatomical model, as illustrated in FIG. 7(C). This figures illustrates that output of an electrophysiology simulation can generate myocardial activation times.

Comparison of Global and Local Cardiac Function

Figure 8:
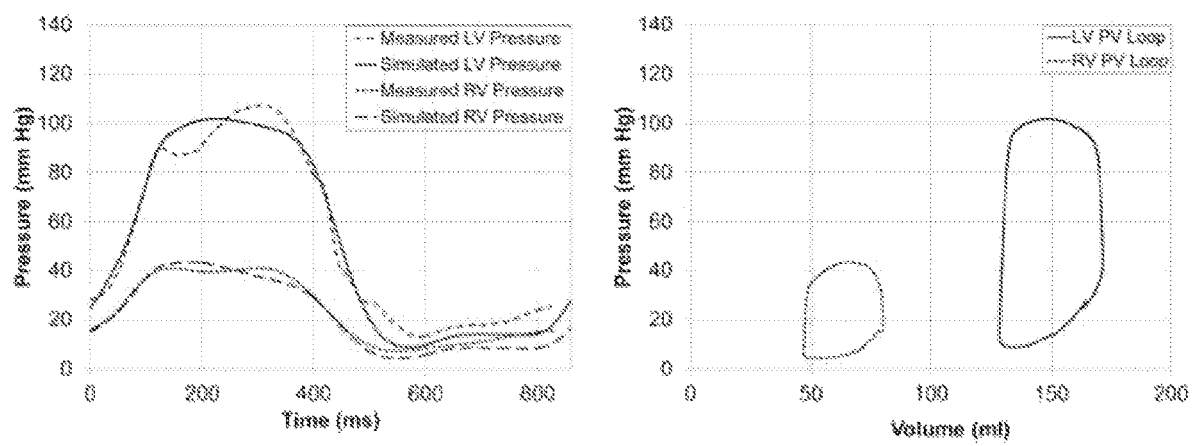
FIGS. 8 and 9 graphically illustrate a comparison of global and local cardiac function.

Model generated pressures and stroke volumes match measured data;

Radial displacement of different segments of the LV match with displacements measured using echocardiographic images FIG. 8 illustrates simulated and measured LV and RV pressure and PV loops, with FIG. 8A measuring pressure as a function of time; and FIG. 8B measuring pressure as a function of volume.

Figure 9:
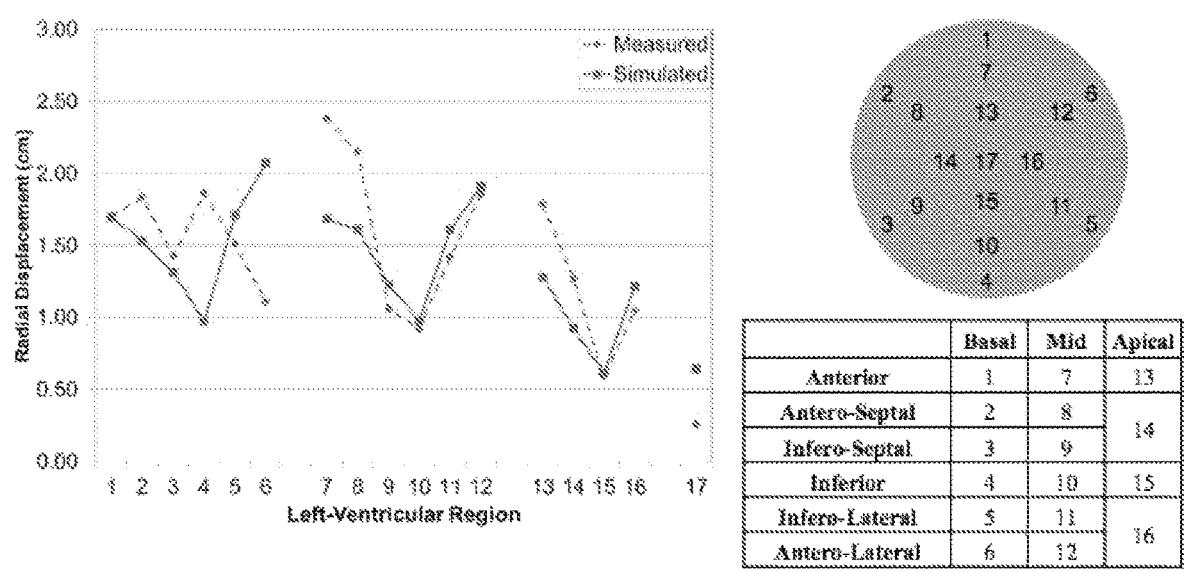

FIG. 9 illustrates radial displacement between end-diastole and end-systole from the measured and simulated geometries, with FIG. 9A measuring (measured and simulated) radial displacement as a function of the left ventricular region; and FIG. 9B graphically and as a table displays the data of FIG. 9A.

FIG. 10 illustrates a comparison of ventricular geometry of the simulated heart (brown), overlaid on the clinical echocardiographic images of the same heart at end-diastole, as illustrated in FIG. 10(A), and end-systole, as illustrated in FIG. 10(A).

Regional Stress-Strain Work Loops

FIG. 11 illustrates stress-strain loops used to compute regional work density; the schematic demonstrates that the septal region performs minimal or negative work in patients who responded better to CRT; FIG. 11(A) illustrates RV free wall stress-strain loops; FIG. 11(B) illustrates septum stress-strain loops; FIG. 11(C) illustrates anterior-posterior and LV free wall stress-strain loops.

Distribution of External Work Density

Figure 12:
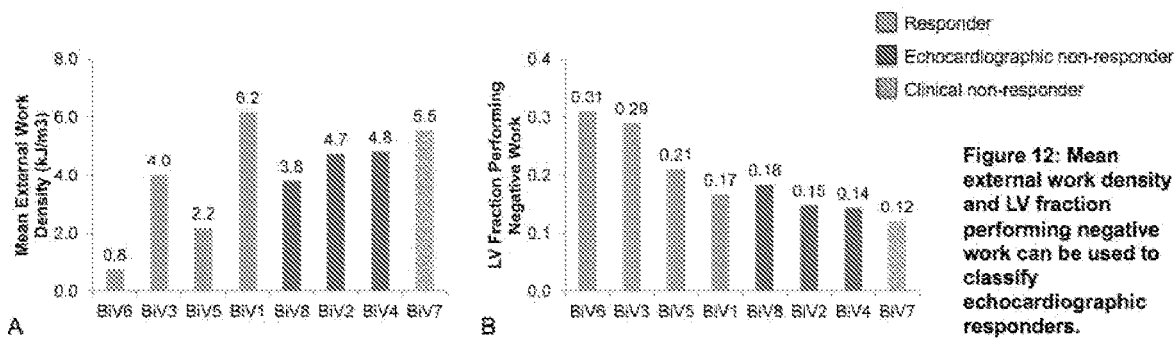
FIG. 12 illustrates mean external work density and LV fraction performing negative work can be used to classify echocardiographic responders; where FIG. 12(A) graphically illustrates the measurement of mean external work density in responders, echocardiographic non-responders and clinical non-responders.

FIG. 12 illustrates mean external work density and LV fraction performing negative work can be used to classify echocardiographic responders; where FIG. 12(A) graphically illustrates the measurement of mean external work density in responders, echocardiographic non-responders and clinical non-responders; and FIG. 12(B) graphically illustrates the measurement of LV fraction performing negative work in the same patient samples as FIG. 12(A).

Classification of Echocardiographic Response

FIG. 13 illustrates receiver-operator characteristic (ROC) curves for using negative LV and septal work as classifiers of echocardiographic response to CRT; the echocardiographic response is classified using 10% reduction in end-systolic volume, as illustrated in FIG. 13(A), or 5% absolute increase in ejection fraction, as illustrated in FIG. 13(B); where FIG. 13(A) graphically illustrates data measuring true positive rate and a function of false positive rate of negative LV work (at 1.00) and negative septal work (at 1.00); and FIG. 13(B) graphically illustrates data measuring true positive rate and a function of false positive rate of negative LV work (at 0.84) and negative septal work (at 0.81).

Biomarkers for Reverse Remodeling

FIG. 14 illustrates that both coefficient of variation of external work density, as illustrated in FIG. 14(A), and fraction of LV performing negative work, as illustrated in FIG. 14(B), can predict quantitative measures of left-ventricular reverse remodeling; this is a strong indication that these abnormally enlarged hearts have decreased in size with prolonged application of CRT, i.e., a successful therapy.

Comprehensive Patient-Specific Computational Models

We have demonstrated the viability of creating detailed patient-specific models to perform electromechanics simulations in DHF patients; models which are capable of realistically replicating patient-specific global and regional cardiac functions as well as local left ventricular wall displacements.

Classification Based on Echocardiographic Response to CRT

Regional work heterogeneity can be used as a sensitive indicator of mechanical dyssynchrony. Fraction of the myocardium performing negative work can be used as a metric of regional work heterogeneity; negative work locations in the left ventricle can further be localized to the septal region in DHF patients; fraction of the LV and septum performing negative work can be used as classifiers to distinguish between echocardiographic responders and non-responders with high accuracy (area under ROC curves >0.8).

Prediction of Reverse Remodeling

Functional improvement following CRT is greatest in patients with the largest region of LV performing negative work; and Left ventricular negative work fraction can quantitatively predict echocardiographic measures of left ventricular reverse remodeling in DHF patients.

In alternative embodiment, exemplary computational patient-specific models of the invention for cardiovascular systems are used to measure model-derived metrics that can better predict CRT response. For example, in one exemplary computational patient-specific models of the invention: in DHF patients, functional improvements in response to CRT are greater in subjects with higher baseline heterogeneity of regional work.

To demonstrate, we developed multi-scale, patient-specific, computational, cardiovascular models that can replicate baseline cardiac function in DHF patients. These exemplary comprehensive finite-element models of the invention take into account detailed patient measurements (such as bi-ventricular geometry, myofiber architecture, cardiac pressures, infarct/scar location, etc.) and replicate both global and local baseline cardiac function. We tested this hypothesis in ten DHF patients (8 with follow-up) who are part of an ongoing CRT study at the VA Hospital, San Diego. We have identified with high correlation that functional improvement following CRT is greatest in patients with the largest region of the left ventricle or septum performing negative work.

This exemplary patient-specific electromechanical model computes the myocardial external work density regional distribution in the ventricle. It has been shown that the degree of mechanical dyssynchrony as measured by indices derived from the regional work distribution correlate with the degree of echocardiographic CRT response (FIG. 14). The myocardial external work density regional distribution is calculated from the model as:

$$W = \oint_{cardiac\ cycle} \Sigma_{i=1}^{3} \Sigma_{i=1}^{3} \sigma_{ij} d\epsilon_{ij}$$

in general, or specifically in these results by the equation:

$$W = \oint_{cardiac\ cycle} \sigma_{ff} d\epsilon_{ff} + \oint_{cardiac\ cycle} \sigma_{cc} d\epsilon_{cc} + \oint_{cardiac\ cycle} \sigma_{ss} d\epsilon_{ss}$$

where sigma and epsilon are Cauchy stress and natural strain in the fiber direction (f), cross-fiber direction (c), and the direction perpendicular to the former two (s). Examples of indices derived from the regional work distribution compute the distribution heterogeneity and total cardiac cycle work.

In this exemplary patient-specific electromechanical model, the coefficient of variation of work (COVW) is a measure of the heterogeneity of the myocardial external work density distribution, and COVW is computed as:

$$COVW = \frac{W_\sigma}{W_\pi}$$

High COVW indicates increased mechanical dyssynchrony. Values for COVW range from 1.0-1.25 for low mechanical dyssynchrony (weak CRT response), 1.25-1.50 for moderate mechanical dyssynchrony (moderate CRT response), and 1.5-1.7 for high mechanical dyssynchrony (strong CRT responders) at baseline (FIG. 14 A).

A local negative value of total cardiac cycle work is a direct measure of local lost pump efficiency. The fraction of the left ventricular mass performing negative work (LVNW) at baseline is indicative of the existing severity of mechanical dyssynchrony. Values for LVNW approximately range from 0.1-0.15 for low mechanical dyssynchrony (weak CRT response), 0.15-0.20 for moderate mechanical dyssynchrony (moderate CRT response), and 0.2-0.25 for high mechanical dyssynchrony (strong CRT response) at baseline (FIG. 14 B).

A causal mechanism of CRT is the recruitment of septal myocardial regions which had originally performed negative work at baseline to perform positive work. The change (positive reduction) in the fraction of septum performing negative work (ASTNW) after CRT is a direct measure of pump function improvement and correlates with positive CRT response. Values for ΔSTNW approximately range from 0 to 0.06 for low improvement (weak CRT response), 0.06 to 0.12 for moderate improvement (moderate CRT response), and 0.12 to 0.18 for high improvement (strong CRT response) (FIG. 14 C).

Four Categories of Model Clinical Utility

In alternative embodiments, the clinical utility of patient-specific electromechanical models of the invention are comprised of four main categories:

1. Diagnostic support

Work heterogeneity metrics can be used as supporting diagnostic measure that can supplement existing diagnostics (such as QRS duration >120 ms, electrocardiographic features, low dP/dT) to characterize dyssynchronous heart failure (DHF). Patients with high work heterogeneity can be classified separately from patients with low work heterogeneity. This can help the clinicians in deciding on the appropriate therapeutic response to different DHF patients by estimating the severity of the existing heart failure using COVW and LVNW.

2. Clinical decision support

The metrics for work heterogeneity can be used as a decision tool for choosing the correct intervention techniques for patients with DHF. Patients having high work heterogeneity (COVW>1.4, LVNW>16%, SNW>25%) at baseline are ideal candidates for CRT. Similarly, CRT may not be effective in patients with low baseline work heterogeneity (COVW<1.2, LVNW<12%, SNW<15%). This can be used as additional information aiding the clinical decision for the intervention technique. Based on the diagnostic, the model may aid in the decision as to whether or not a candidate would likely benefit from undergoing an ICD implantation procedure to apply CRT.

3. Clinical optimization

Modeling the response to different parameters of the CRT intervention helps in optimizing the intervention procedure for a particular patient. Therapeutic parameters and protocols include but are not limited to optimal lead placement and the relative timing of lead stimulus application. Therapeutic outcomes may be predicted by simulation before implantation to estimate the best possible CRT response, as computed by mechanical dyssynchrony indices such as ΔSTNW.

4. Follow-up

Work heterogeneity metrics can be used as follow-up diagnostic measures to assess the success or failure of CRT in a particular patient. A successful CRT procedure may only reduce the end-systolic volume but may also reduce the work heterogeneity. In alternative embodiments, the reduction in work heterogeneity is computed immediately after the procedure, thus providing a faster assessment of the therapy.

FIG. 3 (addendum) summarizes the clinical data, registration methods, and model components.

In alternative embodiments, models for designing methods of the invention are constructed from patient clinical data. The clinical data included:

Digital images of cardiac and thoracic anatomy
  Computed tomography images, magnetic resonance images, diffusion tensor magnetic resonance images, transthoracic echocardiographic images
Ventricular cavity pressures
  Intracardiac catheterization
Electrical activation pattern
  Electrocardiograms, electroanatomic mapping.

In alternative embodiments, the four main components of exemplary patient-specific computer cardiovascular models or methods of the invention are: the anatomy (Anatomic Model), electrophysiology (Electrophysiology Model), biomechanics (Passive Material Model, Active Contraction Model), and hemodynamics (Hemodynamics model) (FIG. 3).

General methods to register the clinical data to the model subcomponents are listed next to the category name in parenthesis, below. Examples of particular methods that can be used to practice the methods of this invention are described, e.g., in Aguado-Sierra et al., 2011; Krishnamurthy et al., 2012; Villongco et al., 2014, see below.

Anatomical Model

Model left and right ventricular geometry from patient cardiac images from MRI, CT, echocardiography or other imaging modalities (Image segmentation and mesh fitting or mesh generation)

Incorporate ventricular muscle fiber architecture using human data from cadaver hearts or other sources (Fiber angle or tensor field fitting, Large deformation diffeomorphic mapping to map fibers to patient-specific geometry)

Model shape and location of myocardial infarcts or ischemic zones from MIBI-SPECT, Gd delayed-enhancement MRI or other clinical data (image segmentation and fitting of patient-specific infarct or ischemic zone geometry). The myocardial infarct or ischemic region is modeled as a region of altered mechanical and electrical properties based on physical alterations associated with ischemia or infarction.

Electrophysiology model

Use an ionic model of the human ventricular action potential adjusted for changes associated with heart failure Model electrical conduction by identifying electrical stimulus location(s) and regional myocardial electrical conductivities of bulk left and right ventricular myocardium, left and right ventricular endocardium, infarct or ischemic tissue making use of patient electrophysiology recordings such as 12-lead ECG (Electrical model parameter optimization to match predicted and measured ECG, VCG or electrical recordings)

Solve for three-dimensional action potential wave propagation to obtain three-dimension al distribution of regional electrical activation times used to trigger mechanical contraction model Biomechanics model Identify patient-specific resting myocardial mechanical properties making use of measured or estimated diastolic ventricular pressures and volumes. Match model passive pressure-volume relation to human measurements, for example, to the normalized relation observed by Klotz et al, Am J Physiol, 2006. Solve for unloaded ventricular geometry making use of measured geometry (typically at end-diastole), known or estimated left ventricular end-diastolic pressure and volume, and a dual or inverse solution (e.g. as given by Krishnamurthy et al., *J Comp Phys*, 2013)

Identify patient-specific active contractile myocardial properties such as peak systolic stiffness, rate of tension development and rate of diastolic tension decline making use of estimated or recorded ventricular and/or arterial blood pressures, and systolic ventricular volume changed. Adjust these parameters or solve for them using numerical optimization methods to minimize the differences between measured and computed ventricular systolic pressures and volume changes.

Hemodynamics model

Formulate and parameterize a closed loop circulation model and identify parameters to match patient measurements of arterial pressure waveforms.

Make use of measured patient recordings including mitral and aortic valve dimensions and mitral regurgitant volume from echocardiography. Solve a numerical optimization or use an adaptive model such as CircAdapt (Arts et al., *Am J Physiol*, 2005).

Integrated model

Couple hemodynamic model to ventricular mechanics model using the algorithm of Kerchoffs et al. (*Ann Biomed Eng*, 2007).

Couple electrical model top biomechanical model by using electrical depolarization times as times for initiation of systolic tension development, or use a fully coupled electromechanical model in which the ionic model includes intracellular calcium transients and a model of myofilament activation to tension development.

Use model to solve for distributions of regional wall motions, pressures, stress and strain throughout the cardiac cycle. Integrate stress strain loops to obtain regional myocardial work density distributions. Derive from distributions predictive indices of heterogeneity including COVW, fraction of myocardium performing negative work or fraction of septum performing negative work (i.e. regions having work performed on them by surrounding regions).

Use the model to simulate possible therapeutic interventions such as cardiac resynchronization using biventricular pacing. Specify pacing lead locations or VV delay times between lead stimuli and adjust these to maximize the decrease in measures of regional myocardial work density heterogeneity, e.g. to eliminate all negative work regions and to reduce the magnitude of work heterogeneity as much as possible.

REFERENCES

1. Aguado-Sierra; J., et al. (2011). Patient-specific modeling of dyssynchronous heart failure: a case study. *Progress in biophysics and molecular biology*, 107(1), 147-155.
2. Kerckhoffs, R. C., et al. (2010). Ventricular dilation and electrical dyssynchrony synergistically increase regional mechanical non-uniformity but not mechanical dyssynchrony a computational model. *Circulation: Heart Failure*, 3(4), 528-536,
3. Krishnamurthy, A., et al. (2013). Patient-specific models of cardiac biomechanics. *Journal of computational physics*, 244, 4-21.
4. Strauss, D. G., et al. (2011). Defining left bundle branch block in the era of cardiac resynchronization therapy. *The American journal of cardiology*, 107(6), 927-934.
5. Villongco, C. T. et al. (2014). Patient-specific modeling of ventricular activation pattern using surface ECG-derived vector-cardiogram in bundle branch block. *Progress in biophysics and molecular biology*.

A number of embodiments of the invention have been described. Nevertheless, it will be understood that various modifications may be made without departing from the spirit and scope of the invention. Accordingly, other embodiments are within the scope of the following claims.

What is claimed is:

1. A method, comprising:
measuring clinical data for a heart associated with dyssynchronous heart failure, the clinical data including an image of a cardiothoracic anatomy, a ventricular cavity pressure, and an electrical activation pattern;

generating, based at least on the measured clinical data, a three-dimensional model of the heart associated with dyssynchronous heart failure, the three-dimensional model simulating a stress and a strain across a plurality of myocardial regions comprising the heart, the stress and the strain being simulated in a fiber direction, a cross-fiber direction, and a direction perpendicular to the fiber direction and the cross-fiber direction;

determining, based at least on the three-dimensional model, a sum of products of a Cauchy stress and natural strain in each of the fiber direction, the cross-fiber direction, and the direction perpendicular to the fiber direction and the cross-fiber direction, the sum of the products of the Cauchy stresses and natural strains corresponding to a distribution of regional work across the plurality of myocardial regions comprising the heart;

generating, based at least on the distribution of regional work across the plurality of myocardial regions, a biomarker comprising a fraction of a mass of the plurality of myocardial regions performing negative work during a cardiac cycle, the biomarker further comprising a coefficient indicative of a variation in a first amount of work being performed by the plurality of myocardial regions and/or a second amount of negative work being performed by the plurality of myocardial regions;

predicting, based at least on the biomarker, a response to a cardiac resynchronization therapy, wherein the predicting includes determining, based at least on a difference in the biomarker associated with each of a plurality of simulations having a different pacing lead location and/or a different ventriculo-ventricular pacing delay time, an amount to which the cardiac resynchronization therapy is likely to affect the dyssynchronous heart failure;

determining a therapeutic parameter based at least on the predicting of the response to the cardiac resynchronization therapy, wherein the therapeutic parameter includes at least one of a pacing lead location or a ventriculo-ventricular pacing delay time; and applying, based on the therapeutic parameter, cardiac resynchronization therapy to the heart to resynchronize the heart.

2. The method of claim 1, wherein the plurality of myocardial regions include a first myocardial region that performs work by contracting, and wherein the plurality of myocardial regions further include a second myocardial region that performs negative work by elongating while the first myocardial region is contracting.

3. The method of claim 2, wherein the coefficient corresponds to a variation in the first amount of work performed by the first myocardial region and the second amount of negative work performed by the second myocardial region.

4. The method of claim 1, wherein the plurality of myocardial regions include at least one of a left ventricle, a right ventricle, and a septum of the heart.

5. The method of claim 4, wherein the biomarker further comprises a myocardial negative work density fraction corresponding to a fraction of a respective mass of the left ventricle, the right ventricle, and the septum performing negative work during the cardiac cycle.

6. The method of claim 1, further comprising:
generating, based at least on the biomarker, a diagnosis for dyssynchronous heart failure.

7. The method of claim 1, further comprising:

determining, based at least on the difference in the biomarker, a parameter for subsequently administering the cardiac resynchronization therapy, the parameter including at least one of a pacing lead location and a ventriculo-ventricular pacing delay time.

8. The method of claim 1, further comprising:
classifying, based at least on the biomarker, the heart as being responsive or non-responsive to cardiac resynchronization therapy.

9. The method of claim 1, wherein the image of the cardiothoracic anatomy comprises one of a computed tomography image, a magnetic resonance image, a diffusion tensor magnetic resonance image, and a transthoracic echocardiographic image.

10. The method of claim 1, wherein the ventricular cavity pressure is determined by at least performing an intracardiac catheterization.

11. The method of claim 1, wherein the electrical activation pattern is determined based on at least one of an electrocardiogram and an electroanatomic mapping.

12. The method of claim 1, wherein the distribution of regional work across the plurality of myocardial regions comprising the heart is determined by applying the equation:

$$W = \oint_{\text{cardiac cycle}} \sigma_{ff} d\varepsilon_{ff} + \oint_{\text{cardiac cycle}} \sigma_{cc} d\varepsilon_{cc} + \oint_{\text{cardiac cycle}} \sigma_{ss} d\varepsilon_{ss}$$

wherein W denotes the distribution of regional work, $\sigma$ denotes the Cauchy stress, $\varepsilon$ denotes the natural strain, $ff$ denotes the fiber direction, $cc$ denotes the cross-fiber direction, and $ss$ denotes the direction perpendicular to the fiber direction and the cross-fiber direction.

13. A system, comprising:
at least one processor; and
at least one memory including program code which when executed by the at least one processor provides operations comprising:

measuring clinical data for a heart associated with dyssynchronous heart failure, the clinical data including an image of a cardiothoracic anatomy, a ventricular cavity pressure, and an electrical activation pattern;

generating, based at least on the measured clinical data, a three-dimensional model of the heart associated with dyssynchronous heart failure, the three-dimensional model simulating a stress and a strain across a plurality of myocardial regions comprising the heart, the stress and the strain being simulated in a fiber direction, a cross-fiber direction, and a direction perpendicular to the fiber direction and the cross-fiber direction;

determining, based at least on the three-dimensional model, a sum of products of a Cauchy stress and natural strain in each of the fiber direction, the cross-fiber direction, and the direction perpendicular to the fiber direction and the cross-fiber direction, the sum of the products of the Cauchy stresses and natural strains corresponding to a distribution of regional work across the plurality of myocardial regions comprising the heart;

generating, based at least on the distribution of regional work across the plurality of myocardial regions, a biomarker comprising a fraction of a mass of the plurality of myocardial regions performing negative work during a cardiac cycle, the biomarker further comprising a coefficient indicative of a variation in a first amount of work being performed by the plurality of myocardial regions and/or a second amount of negative work being performed by the plurality of myocardial regions;

predicting, based at least on the biomarker, a response to a cardiac resynchronization therapy, wherein the predicting includes determining, based at least on a difference in the biomarker associated with each of a plurality of simulations having a different pacing lead location and/or a different ventriculo-ventricular pacing delay time, an amount to which the cardiac resynchronization therapy is likely to affect the dyssynchronous heart failure;

determining a therapeutic parameter based at least on the predicting of the response to the cardiac resynchronization therapy, wherein the therapeutic parameter includes at least one of a pacing lead location or a ventriculo-ventricular pacing delay time; and applying, based on the therapeutic parameter, cardiac resynchronization therapy to the heart to resynchronize the heart.

14. The system of claim 13, wherein the plurality of myocardial regions include a first myocardial region that performs work by contracting, and wherein the plurality of myocardial regions include a second myocardial region that performs negative work by elongating while the first myocardial region is contracting.

15. The system of claim 14, wherein the coefficient corresponds to a variation in the first amount of work performed by the first myocardial region and the second amount of negative work performed by the second myocardial region.

16. The system of claim 13, wherein the plurality of myocardial regions include at least one of a left ventricle, a right ventricle, and a septum of the heart.

17. The system of claim 16, wherein the biomarker further comprises a myocardial negative work density fraction corresponding to a fraction of a respective mass of the left ventricle, the right ventricle, and the septum performing negative work during the cardiac cycle.

18. The system of claim 13, further comprising:
generating, based at least on the biomarker, a diagnosis for dyssynchronous heart failure.

19. The system of claim 13, further comprising:
determining, based at least on the difference in the biomarker, a parameter for subsequently administering the cardiac resynchronization therapy, the parameter including at least one of a pacing lead location and a ventriculo-ventricular pacing delay time.

20. The system of claim 13, further comprising:
classifying, based at least on the biomarker, the heart as being responsive or non-responsive to cardiac resynchronization therapy.

21. A non-transitory computer-readable storage medium including program code which when executed by at least one processor causes operations comprising:

measuring clinical data for a heart associated with dyssynchronous heart failure, the clinical data including an image of a cardiothoracic anatomy, a ventricular cavity pressure, and an electrical activation pattern;

generating, based at least on the measured clinical data, a three-dimensional model of the heart associated with dyssynchronous heart failure, the three-dimensional model simulating a stress and a strain across a plurality of myocardial regions comprising the heart, the stress and the strain being simulated in a fiber direction, a cross-fiber direction, and a direction perpendicular to the fiber direction and the cross-fiber direction;

determining, based at least on the three-dimensional model, a sum of products of a Cauchy stress and natural strain in each of the fiber direction, the cross-fiber direction, and the direction perpendicular to the fiber direction and the cross-fiber direction, the sum of the products of the Cauchy stresses and natural strains corresponding to a distribution of regional work across the plurality of myocardial regions comprising the heart;

generating, based at least on the distribution of regional work across the plurality of myocardial regions, a biomarker comprising a fraction of a mass of the plurality of myocardial regions performing negative work during a cardiac cycle, the biomarker further comprising a coefficient indicative of a variation in a first amount of work being performed by the plurality of myocardial regions and/or a second amount of negative work being performed by the plurality of myocardial regions;

predicting, based at least on the biomarker, a response to a cardiac resynchronization therapy, wherein the predicting includes determining, based at least on a difference in the biomarker associated with each of a plurality of simulations having a different pacing lead location and/or a different ventriculo-ventricular pacing delay time, an amount to which the cardiac resynchronization therapy is likely to affect the dyssynchronous heart failure;

determining a therapeutic parameter based at least on the predicting of the response to the cardiac resynchronization therapy, wherein the therapeutic parameter includes at least one of a pacing lead location or a ventriculo-ventricular pacing delay time; and applying, based on the therapeutic parameter, cardiac resynchronization therapy to the heart to resynchronize the heart.

* * * * *